(12) United States Patent
Ben-David et al.

(10) Patent No.: US 8,204,591 B2
(45) Date of Patent: Jun. 19, 2012

(54) TECHNIQUES FOR PREVENTION OF ATRIAL FIBRILLATION

(75) Inventors: Tamir Ben-David, Tel Aviv (IL); Omry Ben-Ezra, Tel Aviv (IL); Ehud Cohen, Ganei Tikva (IL)

(73) Assignee: Bio Control Medical (B.C.M.) Ltd., Yahud (IL)

( * ) Notice: Subject to any disclaimer, the term of this patent is extended or adjusted under 35 U.S.C. 154(b) by 835 days.

(21) Appl. No.: 11/657,784

(22) Filed: Jan. 24, 2007

(65) Prior Publication Data
US 2007/0179543 A1 Aug. 2, 2007

Related U.S. Application Data

(63) Continuation-in-part of application No. 10/866,601, filed on Jun. 10, 2004, now abandoned, and a continuation-in-part of application No. 11/234,877, filed on Sep. 22, 2005, now Pat. No. 7,885,709, which is a continuation-in-part of application No. 11/064,446, filed on Feb. 22, 2005, now Pat. No. 7,974,693, which is a continuation-in-part of application No. 11/062,324, filed on Feb. 18, 2005, now Pat. No. 7,634,317, which is a continuation-in-part of application No. 10/719,659, filed on Nov. 20, 2003, now Pat. No. 7,778,711, which is a continuation-in-part of application No. PCT/IL03/00431, filed on May 23, 2003, which is a continuation-in-part of application No. 10/205,475, filed on Jul. 24, 2002, now Pat. No. 7,778,703, and a continuation-in-part of application No. 10/560,654, filed as application No. PCT/IL2004/000496 on Jun. 10, 2004, now Pat. No. 7,885,711, which is a continuation-in-part of application No. 10/461,696, filed on Jun. 13, 2003, now Pat. No. 7,321,793, and a continuation-in-part of application No. 11/359,266, filed on Feb. 21, 2006, now Pat. No. 8,036,745, and a continuation-in-part of application No. 10/866,601, filed on Jun. 10, 2004, now abandoned.

(60) Provisional application No. 60/478,576, filed on Jun. 13, 2003, provisional application No. 60/383,157, filed on May 23, 2002, provisional application No. 60/612,428, filed on Sep. 23, 2004, provisional application No. 60/668,275, filed on Apr. 4, 2005, provisional application No. 60/655,604, filed on Feb. 22, 2005.

(51) Int. Cl.
*A61N 1/36* (2006.01)

(52) U.S. Cl. ........... 607/14; 607/1; 607/2; 607/5; 607/7; 607/9; 607/11; 607/15; 607/115; 607/116; 607/117; 607/118

(58) Field of Classification Search .................. 607/1–2, 607/5, 7, 9, 11, 14–15, 115–118
See application file for complete search history.

(56) References Cited

U.S. PATENT DOCUMENTS 3,411,507 A 11/1968 Wingrove
(Continued)

FOREIGN PATENT DOCUMENTS

EP 0688577 12/1995
(Continued)

OTHER PUBLICATIONS

Office Action, issued Feb. 5, 2010, in connection with U.S. Appl. No. 11/974,951, filed Oct. 16, 2007.

(Continued)

*Primary Examiner* — Carl H Layno
*Assistant Examiner* — Deborah Malamud
(74) *Attorney, Agent, or Firm* — Sughrue Mion, PLLC

(57) ABSTRACT

A method is provided, including identifying that a subject is at risk of suffering from atrial fibrillation (AF). Responsively to the identifying, a risk of an occurrence of an episode of the AF is reduced by applying an electrical current to a site of the subject selected from the group consisting of: a vagus nerve, a sinoatrial (SA) node fat pad, a pulmonary vein, a carotid artery, a carotid sinus, a coronary sinus, a vena cava vein, a jugular vein, an azygos vein, an innominate vein, and a subclavian vein, and configuring the current to stimulate autonomic nervous tissue in the site. Other embodiments are also described.

27 Claims, 5 Drawing Sheets

U.S. PATENT DOCUMENTS

| | | | |
|---|---|---|---|
| 4,019,518 A | 4/1977 | Maurer et al. | |
| 4,161,952 A | 7/1979 | Kinney et al. | |
| 4,392,496 A | 7/1983 | Stanton | |
| 4,535,785 A | 8/1985 | Honert | |
| 4,559,948 A | 12/1985 | Liss et al. | |
| 4,573,481 A | 3/1986 | Bullara | |
| 4,585,005 A | 4/1986 | Lue et al. | |
| 4,602,624 A | 7/1986 | Naples et al. | |
| 4,608,985 A | 9/1986 | Crish et al. | |
| 4,628,942 A | 12/1986 | Sweeney et al. | |
| 4,632,116 A | 12/1986 | Rosen | |
| 4,649,936 A | 3/1987 | Ungar et al. | |
| 4,663,102 A | 5/1987 | Brenman et al. | |
| 4,702,254 A | 10/1987 | Zabara | |
| 4,739,764 A | 4/1988 | Lue et al. | |
| 4,867,164 A | 9/1989 | Zabara | |
| 4,922,908 A | 5/1990 | Morawetz et al. | |
| 4,926,865 A | 5/1990 | Oman | |
| 4,962,751 A | 10/1990 | Krauter | |
| 5,025,807 A | 6/1991 | Zabara | |
| 5,042,497 A | 8/1991 | Shapland | |
| 5,058,599 A | 10/1991 | Andersen | |
| 5,069,680 A | 12/1991 | Grandjean | |
| 5,139,020 A | 8/1992 | Koestner et al. | |
| 5,170,802 A | 12/1992 | Mehra | |
| 5,178,161 A | 1/1993 | Kovacs | |
| 5,188,104 A | 2/1993 | Wernicke et al. | |
| 5,199,428 A | 4/1993 | Obel et al. | |
| 5,199,430 A | 4/1993 | Fang et al. | |
| 5,203,326 A | 4/1993 | Collins | |
| 5,205,285 A | 4/1993 | Baker | |
| 5,215,086 A | 6/1993 | Terry et al. | |
| 5,224,491 A | 7/1993 | Mehra | |
| 5,231,988 A | 8/1993 | Wernicke et al. | |
| 5,243,980 A | 9/1993 | Mehra | |
| 5,263,480 A | 11/1993 | Wernicke et al. | |
| 5,282,468 A | 2/1994 | Klepinski | |
| 5,292,344 A | 3/1994 | Douglas | |
| 5,299,569 A | 4/1994 | Wernicke et al. | |
| 5,314,495 A | 5/1994 | Kovacs | |
| 5,330,507 A | 7/1994 | Schwartz et al. | |
| 5,334,221 A | 8/1994 | Bardy | |
| 5,335,657 A | 8/1994 | Terry et al. | |
| 5,356,425 A | 10/1994 | Bardy et al. | |
| 5,411,531 A | 5/1995 | Hill et al. | |
| 5,423,872 A | 6/1995 | Cigaina | |
| 5,437,285 A | 8/1995 | Verrier et al. | |
| 5,439,938 A | 8/1995 | Snyder et al. | |
| 5,454,840 A | 10/1995 | Krakovsky et al. | |
| 5,487,756 A | 1/1996 | Kallesoe | |
| 5,507,784 A | 4/1996 | Hill et al. | |
| 5,522,854 A | 6/1996 | Ideker et al. | |
| 5,540,730 A | 7/1996 | Terry et al. | |
| 5,540,734 A | 7/1996 | Zabara | |
| 5,562,595 A | 10/1996 | Neisz | |
| 5,562,718 A | 10/1996 | Palermo | |
| 5,571,150 A | 11/1996 | Wernicke et al. | |
| 5,578,061 A | 11/1996 | Stroetmann et al. | |
| 5,615,684 A | 4/1997 | Hagel et al. | |
| 5,634,462 A | 6/1997 | Tyler et al. | |
| 5,645,570 A | 7/1997 | Corbucci | |
| 5,658,318 A | 8/1997 | Stroetmann et al. | |
| 5,690,681 A | 11/1997 | Geddes et al. | |
| 5,690,691 A | 11/1997 | Chen | |
| 5,700,282 A | 12/1997 | Zabara | |
| 5,707,400 A | 1/1998 | Terry et al. | |
| 5,711,316 A | 1/1998 | Elsberry et al. | |
| 5,716,385 A | 2/1998 | Mittal et al. | |
| 5,755,750 A | 5/1998 | Petruska et al. | |
| 5,824,027 A | 10/1998 | Hoffer et al. | |
| 5,832,932 A | 11/1998 | Elsberry et al. | |
| 5,833,709 A | 11/1998 | Rise et al. | |
| 5,836,994 A | 11/1998 | Bourgeois | |
| 5,916,239 A * | 6/1999 | Geddes et al. | 607/14 |
| 5,938,584 A | 8/1999 | Ardito et al. | |
| 6,006,134 A | 12/1999 | Hill et al. | |
| 6,026,326 A | 2/2000 | Bardy | |
| 6,058,328 A | 5/2000 | Levine | |
| 6,058,331 A | 5/2000 | King et al. | |
| 6,066,163 A | 5/2000 | John | |
| 6,073,048 A | 6/2000 | Kieval et al. | |
| 6,086,525 A | 7/2000 | Davey et al. | |
| 6,091,977 A | 7/2000 | Tarjan et al. | |
| 6,091,992 A | 7/2000 | Bourgeois | |
| 6,094,598 A | 7/2000 | Elsberry et al. | |
| 6,097,984 A | 8/2000 | Douglas | |
| 6,104,955 A | 8/2000 | Bourgeois | |
| 6,104,956 A | 8/2000 | Naritoku et al. | |
| 6,104,960 A | 8/2000 | Duysens et al. | |
| 6,119,516 A | 9/2000 | Hock | |
| H1905 H | 10/2000 | Hill | |
| 6,134,470 A | 10/2000 | Hartlaub | |
| 6,146,335 A | 11/2000 | Gozani | |
| 6,161,029 A | 12/2000 | Spreigl et al. | |
| 6,167,304 A | 12/2000 | Loos | |
| 6,169,924 B1 | 1/2001 | Meloy et al. | |
| 6,195,584 B1 | 2/2001 | Hill et al. | |
| 6,205,359 B1 | 3/2001 | Boveja | |
| 6,230,061 B1 | 5/2001 | Hartung | |
| 6,240,314 B1 | 5/2001 | Plicchi et al. | |
| 6,266,564 B1 | 7/2001 | Hill | |
| 6,272,377 B1 | 8/2001 | Sweeney et al. | |
| 6,292,695 B1 | 9/2001 | Webster et al. | |
| 6,319,241 B1 | 11/2001 | King et al. | |
| 6,341,236 B1 | 1/2002 | Osorio et al. | |
| 6,356,784 B1 | 3/2002 | Lozano et al. | |
| 6,366,813 B1 | 4/2002 | Dilorenzo | |
| 6,381,499 B1 | 4/2002 | Taylor et al. | |
| 6,400,982 B2 | 6/2002 | Sweeney et al. | |
| 6,405,079 B1 | 6/2002 | Ansarinia | |
| 6,434,424 B1 | 8/2002 | Igel et al. | |
| 6,449,507 B1 | 9/2002 | Hill et al. | |
| 6,456,866 B1 | 9/2002 | Tyler | |
| 6,463,328 B1 | 10/2002 | John | |
| 6,473,644 B1 | 10/2002 | Terry et al. | |
| 6,477,406 B1 | 11/2002 | Turcott | |
| 6,493,585 B2 | 12/2002 | Plicchi et al. | |
| 6,511,500 B1 | 1/2003 | Rahme et al. | |
| 6,522,926 B1 | 2/2003 | Kieval et al. | |
| 6,542,774 B2 | 4/2003 | Hill et al. | |
| 6,564,096 B2 | 5/2003 | Mest et al. | |
| 6,571,122 B2 | 5/2003 | Schroeppel et al. | |
| 6,587,727 B2 | 7/2003 | Osorio et al. | |
| 6,600,956 B2 | 7/2003 | Maschino et al. | |
| 6,610,713 B2 | 8/2003 | Tracey | |
| 6,622,041 B2 | 9/2003 | Terry et al. | |
| 6,628,987 B1 | 9/2003 | Hill et al. | |
| 6,668,191 B1 | 12/2003 | Boveja | |
| 6,671,556 B2 | 12/2003 | Osorio et al. | |
| 6,684,105 B2 | 1/2004 | Cohen | |
| 6,690,971 B2 | 2/2004 | Schauerte et al. | |
| RE38,705 E | 2/2005 | Hill et al. | |
| 6,865,416 B2 | 3/2005 | Dev et al. | |
| 6,885,888 B2 | 4/2005 | Rezai et al. | |
| 6,895,280 B2 | 5/2005 | Meadows et al. | |
| 6,907,293 B2 | 6/2005 | Grill et al. | |
| 6,907,295 B2 | 6/2005 | Gross et al. | |
| 6,928,320 B2 | 8/2005 | King | |
| 6,934,583 B2 | 8/2005 | Weinberg et al. | |
| 6,985,774 B2 | 1/2006 | Kieval et al. | |
| 7,050,846 B2 | 5/2006 | Sweeney et al. | |
| 7,076,299 B2 | 7/2006 | Thong | |
| 7,136,700 B1 | 11/2006 | Province | |
| 7,142,917 B2 | 11/2006 | Fukui et al. | |
| 7,321,793 B2 | 1/2008 | Ben Ezra et al. | |
| 7,403,819 B1 | 7/2008 | Shelchuk et al. | |
| 7,765,000 B2 | 7/2010 | Zhang et al. | |
| 7,778,711 B2 | 8/2010 | Ben-David et al. | |
| 2002/0035335 A1 | 3/2002 | Schauerte | |
| 2002/0107553 A1 | 8/2002 | Hill et al. | |
| 2002/0120304 A1 | 8/2002 | Mest | |
| 2003/0018367 A1 | 1/2003 | DiLorenzo | |
| 2003/0040774 A1 | 2/2003 | Terry et al. | |
| 2003/0045909 A1 | 3/2003 | Gross et al. | |
| 2003/0050677 A1 | 3/2003 | Gross et al. | |
| 2003/0078623 A1 | 4/2003 | Weinberg et al. | |
| 2003/0100924 A1 | 5/2003 | Foreman et al. | |

| | | |
|---|---|---|
| 2003/0144709 A1 | 7/2003 | Zabara et al. |
| 2003/0195574 A1 | 10/2003 | Osorio et al. |
| 2003/0212440 A1 | 11/2003 | Boveja et al. |
| 2003/0216775 A1 | 11/2003 | Hill et al. |
| 2003/0236558 A1 | 12/2003 | Whitehurst et al. |
| 2004/0048795 A1 | 3/2004 | Ivanova et al. |
| 2004/0059392 A1 | 3/2004 | Parramon et al. |
| 2004/0138721 A1 | 7/2004 | Osorio et al. |
| 2004/0152958 A1 | 8/2004 | Frei et al. |
| 2004/0158119 A1 | 8/2004 | Osorio et al. |
| 2004/0162594 A1 | 8/2004 | King |
| 2004/0172075 A1 | 9/2004 | Shafer et al. |
| 2004/0199210 A1 | 10/2004 | Shelchuk |
| 2004/0243182 A1 | 12/2004 | Cohen et al. |
| 2004/0249416 A1 | 12/2004 | Yun et al. |
| 2005/0065553 A1 | 3/2005 | Ben Ezra et al. |
| 2005/0131467 A1 | 6/2005 | Boveja et al. |
| 2005/0143787 A1 | 6/2005 | Boveja et al. |
| 2005/0187584 A1 | 8/2005 | Denker et al. |
| 2005/0197675 A1 | 9/2005 | Ben-David et al. |
| 2005/0222644 A1 | 10/2005 | Killian et al. |
| 2005/0267542 A1 | 12/2005 | Ben-David et al. |
| 2006/0015153 A1 | 1/2006 | Gliner et al. |
| 2006/0047325 A1 | 3/2006 | Thimineur et al. |
| 2006/0064140 A1 | 3/2006 | Whitehurst et al. |
| 2006/0074450 A1 | 4/2006 | Boveja |
| 2006/0100668 A1 | 5/2006 | Ben-David |
| 2006/0129205 A1 | 6/2006 | Boveja |
| 2006/0149337 A1 | 7/2006 | John et al. |
| 2006/0167498 A1 | 7/2006 | DiLorenzo et al. |
| 2006/0206155 A1 | 9/2006 | Ben-David et al. |
| 2006/0271115 A1 | 11/2006 | Ben-Ezra et al. |
| 2007/0021786 A1 | 1/2007 | Parnis et al. |
| 2007/0179543 A1 | 8/2007 | Ben-David et al. |

FOREIGN PATENT DOCUMENTS

| | | |
|---|---|---|
| EP | 0831954 | 4/1998 |
| EP | 1785160 | 5/2007 |
| WO | 0110375 | 2/2001 |
| WO | 0110432 | 2/2001 |
| WO | 0126729 | 4/2001 |
| WO | 02085448 | 10/2002 |
| WO | 2004110550 | 12/2004 |
| WO | 2006057734 | 6/2006 |
| WO | 2006102370 | 9/2006 |
| WO | 2007113775 | 10/2007 |

OTHER PUBLICATIONS

Office Action, issued Mar. 15, 2010, in connection with U.S. Appl. No. 11/724,899, filed Mar. 16, 2007.

Office Action, issued Apr. 6, 2010, in connection with U.S. Appl. No. 11/977,291, filed Oct. 23, 2007.

Office Action issued Apr. 5, 2007 during the prosecution of Applicants' U.S. Appl. No. 10/488,334.

Van den Honert, C. et al., (1979) "Generation of unidirectionally propagated action potentials in a peripheral nerve by brief stimuli," Science, vol. 206: 1311-1312.

Office Action issued Aug. 6, 2009, in connection with U.S. Appl. No. 10/205,475, filed Jul. 24, 2002.

Office Action issued Jul. 21, 2009, in connection with U.S. Appl. No. 11/070,842, filed Feb. 24, 2005.

Office Action issued Jul. 23, 2009, in connection with U.S. Appl. No. 11/724,899, filed Mar. 16, 2007.

Office Action issued Aug. 21, 2009, in connection with U.S. Appl. No. 11/975,240, filed Oct. 17, 2007.

Office Action issued Aug. 21, 2009, in connection with U.S. Appl. No. 11/975,169, filed Oct. 17, 2009.

Office Action issued Aug. 25, 2009, in connection with U.S. Appl. No. 11/975,241, filed Oct. 17, 2007.

Office Action issued Jun. 24, 2009 in connection with U.S. Appl. No. 11/978,379, filed Oct. 29, 2007.

Morillo et al., "Chronic Rapid Atrial Pacing. Structural, functional, and electrophysiological characteristics of a new model of sustained atrial fibrillation," Circulation, 1995, 91(5), 1588-1595.

U.S. Appl. No. 60/383,157, filed May 23, 2002, Ayal et al.

U.S. Appl. No. 60/478,576, filed Jun. 13, 2003, Ben Ezra et al.

U.S. Appl. No. 60/612,428, filed Sep. 23, 2004, Ben Ezra et al.

U.S. Appl. No. 60/655,604, filed Feb. 22, 2005, Ben David et al.

U.S. Appl. No. 60/668,275, filed Apr. 4, 2005, Ben David et al.

Office Action, issued Oct. 12, 2010 in connection with U.S. Appl. No. 11/974,951, filed Oct. 16, 2007.

Office Action, issued Oct. 27, 2010 in connection with U.S. Appl. No. 11/977,291, filed Oct. 23, 2007.

An Official Action dated Feb. 4, 2011, which issued during the prosecution of Applicant's U.S. Appl. No. 11/974,951.

Bibevski, S. And Dunlap, M.E., (1999) "Ganglionic Mechanisms Contribute to Diminished Vagal Control in Heart Failure," Circulation, 99(22): 2958-63.

Bilgutay, A.M. et al., (1968) "Vagal Tuning. A New Concept in the Treatment of Supreventricular Arrhythmia, Angina Pectoris, and Heart Failure," The Journal of Thoracic and Cardiovascular Surgery, 56(1): 71-82.

Bluemel, K.M. et al., (1990) "Parasympathetic Postganglionic Pathways to the Sinoatrial Node," The American Journal of Physiology, 259(5 Pt 2):H1504-10.

Carlson, M.D. et al., (1992) "Selective Stimulation of Parasympathetic Nerve Fibers to the Human Sinoatrial Node," Circulation, 85: 1311-1317.

Chen, S. et al., (1998) "Intracardiac Stimulation of Human Parasympathetic Nerve Fibers Induces Negative Dromotropic Effects: Implication with the Lesions of Radiofrequency Catheter Ablation," Journal of Cardiovascular Electrophysiology, 9(3): 245-52.

Cooper, T.B. et al., (1980) "Neural Effects on Sinus Rate and Atrioventricular Conduction Produced by Electrical Stimulation from a Transvenous Electrode Catheter in the Canine Right Pulmonary Artery," Circulation Research, 46: 48-57.

Cummings, J.E. et al., (1980) "Preservation of the Anterior Fat Pad Paradoxically Decreases the Incidence of Postoperative Atrial Fibrillation in Humans," Journal of the American College of Cardiology, 43(6): 994-1000.

European Search Report issued by the European Patent Office in connection with European Application No. EP 7253557, issued Jan. 28, 2008 (BioControl Medical Ltd.).

Friedrichs, G., (2000) "Experimental Models of Trial Fibrillation/Flutter," Journal of Pharmacological and Toxicological Methods, 43: 117-123.

Furukawa, Y. et al., (1989) "Differential Blocking Effects of Atropine and Gallamine on Negative Chronotropic and Dromotropic Responses to Vagus Stimulation in Anesthetized Dogs," Journal of Pharmacology and Experimental Therapeutics, 251(3): 797-802.

Fuster, V. and Ryden, L.E., (2001) "ACC/AHA/ESC Guidelines for the Management of Patients with Atrial Fibrillation," Journal of the American College of Cardiology, 38(4): 1231-66.

Garrigue, S. et al., (1998) "Post-ganglionic Vagal Stimulation of the Atrioventricular Node Reduces Ventricular Rate During Atrial Fibrillation," Pacing and Clinical Electrophysiology, 21(4), Part II, 878.

Goldberger, J.J. et al., (1999) "New Technique for Vagal Nerve Stimulation," Journal of Neuroscience Methods, 91(1-2): 109-114.

Hjalmarson, A., (1999) "Prevention of Sudden Cardiac Death with Beta Blockers," Clinical Cardiology, 22 Suppl 5: V11-5.

Jideus, L., (2001) "Atrial Fibrillation After Coronary Artery Bypass Surgery. A Study of Causes and Risk Factors," Comprehensive Summaries of Uppsala Dissertations from the Faculty of Medicine, 1093: 1-56.

Jones, (1995) "Heart Rate Responses to Selective Stimulation of Cardiac Vagal C Fibres in Anaesthetized Cats, Rats and Rabbits," Journal of Physiology, 489.1: 203-214.

Jones, (1998) "Activity of C Fibre Cardiac Vagal Efferents in Anaesthetized Cats and Rats," Journal of Physiology, 507.3: 869-880.

Kwan, H. et al., (2001) "Cardiovascular Adverse Drug Reactions During Initiation of Antiarrhythmic Therapy for Atrial Fibrillation," Canadian Journal of Hospital Pharmacists, 54(1): 10-14.

Li, D. et al., (1999) "Promotion of Atrial Fibrillation by Heart Failure in Dogs. Atrial Remodeling of a Different Sort," Circulation, 100(1): 87-95.

Manfredi, M., (1970) "Differential Block of Conduction of Larger Fibers in Peripheral Nerve by Direct Current," *Archives italiennes de biologie*, 108(1): 52-71.

Office Action issued Nov. 1, 2007 during the prosecution of Applicants' U.S. Appl. No. 10/205,475.

Pagé, P.L. et al., (1995) "Regional Distribution of Atrial Electrical Changes Induced by Stimulation of Extracardiac and Intracardiac Neural Elements," *The Journal of Thoracic and Cardiovascular Surgery*, 109(2): 377-88.

Rijkhoff, N.J.M. And Sinkjær, T., (1999) "Selective Stimulation of Small Diameter Nerve Fibers in a Mixed Bundle," *Proceedings of The Annual Project Meeting Sensations/Neuros and Mid Term Review Meeting Neuros*, p. 20-21.

Schaldach, M., (1992) "New Concepts in Electrotherapy of the Heart," *Electrotherapy of the Heart*, Springer Verlag Heidelberg, p. 210-214.

Waninger, M.S. et al., (2000) "Electrophysiological Control of Ventricular Rate During Atrial Fibrillation," *Pacing and Clinical Physiology*, 23(8): 1239-44.

Zhang, Y. et al., (2002) "Optimal Ventricular Rate Slowing During Atrial Fibrillation by Feedback AV Nodal-Selective Vagal Stimulation," *American Journal of Physiology: Heart and Circulatory Physiology*, 282(3): H1102-10.

1 Mazgalev, T.N., "AV Nodal Physiology," Heart Rhythm Society, www.HRSonline.org.

* cited by examiner

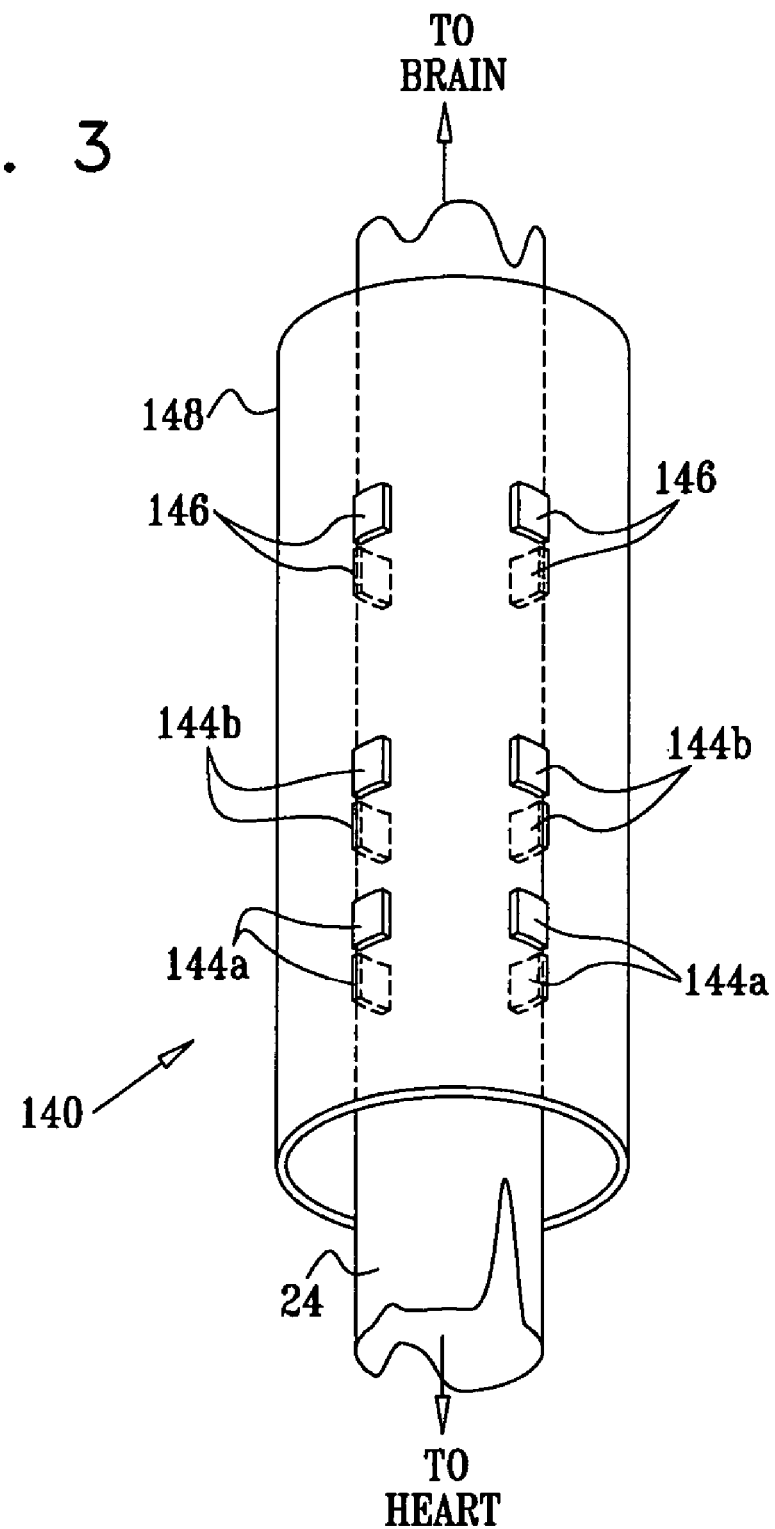

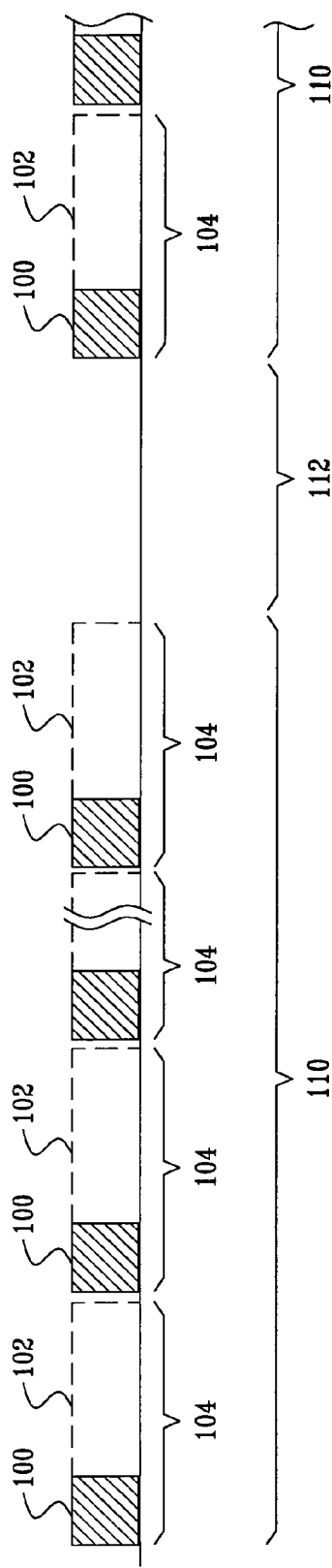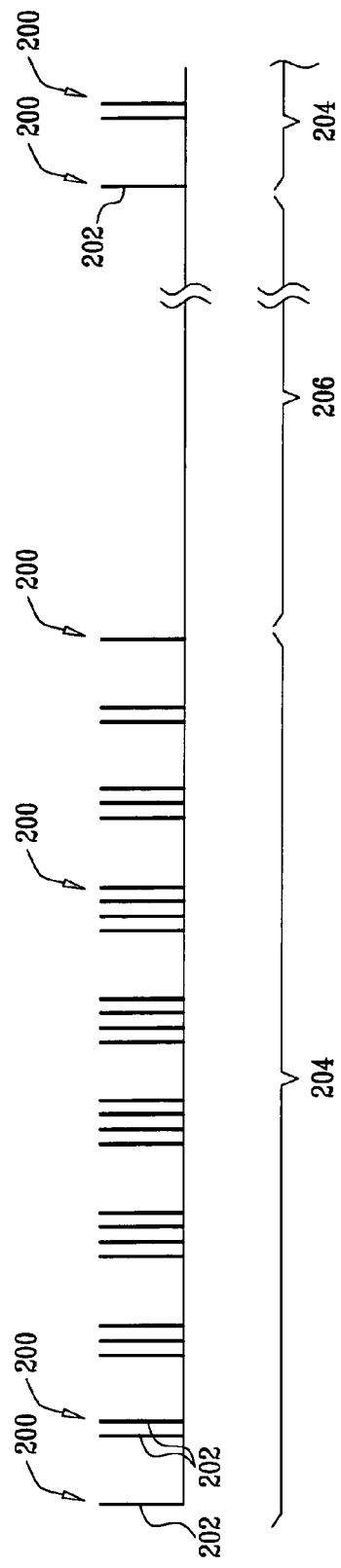

TECHNIQUES FOR PREVENTION OF ATRIAL FIBRILLATION

CROSS-REFERENCES TO RELATED APPLICATIONS

This application is a continuation-in-part of:
(a) U.S. Ser. No. 10/866,601, filed Jun. 10, 2004 now abandoned, which claims the benefit of U.S. Provisional Application No. 60/478,576, filed Jun. 13, 2003;
(b) U.S. Ser. No. 11/234,877, filed Sep. 22, 2005 now U.S. Pat. No. 7,885,709, which:
  (1) is a continuation-in-part of U.S. Ser. No. 11/064,446, filed Feb. 22, 2005 now U.S. Pat. No. 7,974,693, which is a continuation-in-part of U.S. Ser. No. 11/062,324, filed Feb. 18, 2005 now U.S. Pat. No. 7,634,317, which is a continuation-in-part of U.S. Ser. No. 10/719,659, filed Nov. 20, 2003 now U.S. Pat. No. 7,778,711, which is a continuation-in-part of PCT International Application No. PCT/IL2003/00431, filed May 23, 2003, which:
    (i) is a continuation-in-part of U.S. Ser. No. 10/205,475, filed Jul. 24, 2002 now U.S. Pat. No. 7,778,703; and
    (ii) claims the benefit of U.S. Provisional Application No. 60/383,157, filed May 23, 2002, and
  (2) claims the benefit of:
    (i) U.S Provisional Application No. 60/612,428, filed Sep. 23, 2004; and
    (ii) U.S. Provisional Application No. 60/668,275, filed Apr. 4, 2005;
(c) U.S. Ser. No. 10/560,654, filed May 1, 2006 now U.S. Pat. No. 7,885,711 which is the §371 National Stage of PCT International Application PCT/IL2004/00496, filed Jun. 10, 2004, which is a continuation-in-part of U.S. Ser. No. 10/461,696, filed Jun. 13, 2003 now U.S. Pat. No. 7,321,793; and
(d) U.S. Ser. No. 11/359,266, filed Feb. 21, 2006 now U.S. Pat. No. 8,036,745, which: (1) claims the benefit of U.S. Provisional Application No. 60/655,604, filed Feb. 22, 2005, and (2) is a continuation-in-part of U.S. Ser. No. 10/866,601, filed Jun. 10, 2004 now abandoned, the contents of each of which is hereby incorporated by reference herein.

All of the above-mentioned applications are assigned to the assignee of the present application, and are incorporated herein by reference.

FIELD OF THE INVENTION

The present invention relates generally to treating patients by application of electrical signals to selected tissue, and specifically to methods and apparatus for stimulating tissue for treating patients suffering from conditions such as atrial fibrillation.

BACKGROUND OF THE INVENTION

The use of nerve stimulation for treating and controlling a variety of medical, psychiatric, and neurological disorders has seen significant growth over the last several decades, including for treatment of heart conditions. In particular, stimulation of the vagus nerve (the tenth cranial nerve, and part of the parasympathetic nervous system) has been the subject of considerable research. The vagus nerve is composed of somatic and visceral afferents (inward conducting nerve fibers, which convey impulses toward the brain) and efferents (outward conducting nerve fibers, which convey impulses to an effector to regulate activity such as muscle contraction or glandular secretion).

The rate of the heart is restrained in part by parasympathetic stimulation from the right and left vagus nerves. Low vagal nerve activity is considered to be related to various arrhythmias, including tachycardia, ventricular accelerated rhythm, and atrial fibrillation with rapid ventricular response. By artificially stimulating the vagus nerves, it is possible to slow the heart, allowing the heart to more completely relax and the ventricles to experience increased filling. With larger diastolic volumes, the heart may beat more efficiently because it may expend less energy to overcome the myocardial viscosity and elastic forces of the heart with each beat.

Stimulation of the vagus nerve has been proposed as a method for treating various heart conditions, including atrial fibrillation and heart failure. Atrial fibrillation is a condition in which the atria of the heart fail to continuously contract in synchrony with the ventricles of the heart. During fibrillation, the atria undergo rapid and unorganized electrical depolarization, so that no contractile force is produced. The ventricles, which normally receive contraction signals from the atria (through the atrioventricular (AV) node), are inundated with signals, typically resulting in a rapid and/or irregular ventricular rate. Because of this rapid and irregular rate, the patient suffers from reduced cardiac output and/or a feeling of palpitations.

Current therapy for atrial fibrillation includes cardioversion and rate control. Cardioversion is the conversion of the abnormal atrial rhythm into normal sinus rhythm. This conversion is generally achieved pharmacologically or electrically. Rate control therapy is used to control the ventricular rate, while allowing the atria to continue fibrillation. This is generally achieved by slowing the conduction of signals through the AV node from the atria to the ventricles.

After cardioversion has been successfully performed, drug therapy is sometimes indicated for sinus rhythm maintenance or ventricular rate control (see Fuster et al., in their articles cited hereinbelow). Commonly used antiarrhythmic drugs for prophylactic maintenance of sinus rhythm include beta-blockers, amiodarone, disopyramide, dofetilide, flecainide, procainamide, propafenone, quinidine, and sotalol. Potential adverse effects of these drugs include hypotension, bradycardia, QT prolongation, ventricular proarrhythmia (ventricular tachycardia, including torsades de pointes), postural hypotension, and GI complaints, such as diarrhea. For ventricular rate control, commonly used drugs include beta-blockers (e.g., esmolol), calcium channel antagonists (e.g., verapamil, diltiazem) and digoxin. Potential adverse effects of these drugs include hypotension, heart block, heart failure, and bradycardia.

Bilgutay et al., in "Vagal tuning: a new concept in the treatment of supraventricular arrhythmias, angina pectoris, and heart failure," J. Thoracic Cardiovas. Surg. 56(1):71-82, July, 1968, which is incorporated herein by reference, studied the use of a permanently-implanted device with electrodes to stimulate the right vagus nerve for treatment of supraventricular arrhythmias, angina pectoris, and heart failure. Experiments were conducted to determine amplitudes, frequencies, wave shapes and pulse lengths of the stimulating current to achieve slowing of the heart rate. The authors additionally studied an external device, triggered by the R-wave of the electrocardiogram (ECG) of the subject to provide stimulation only upon an achievement of a certain heart rate. They found that when a pulsatile current with a frequency of ten pulses per second and 0.2 milliseconds pulse duration was applied to the vagus nerve, the heart rate could be decreased to half the resting rate while still preserving sinus rhythm. Low amplitude vagal stimulation was employed to control induced tachycardias and ectopic beats. The authors further studied the use of the implanted device in conjunction with the administration of Isuprel, a sympathomimetic drug. They found that Isuprel retained its inotropic effect of increasing contractility, while its chronotropic effect was controlled by the vagal stimulation: "An increased end diastolic volume brought about by slowing of the heart rate by vagal tuning, coupled with increased contractility of the heart induced by the inotropic effect of Isuprel, appeared to increase the efficiency of cardiac performance" (p. 79).

The effect of vagal stimulation on heart rate and other aspects of heart function, including the relationship between the timing of vagal stimulation within the cardiac cycle and the induced effect on heart rate, has been studied in animals. For example, Zhang Y et al., in "Optimal ventricular rate slowing during atrial fibrillation by feedback AV nodal-selective vagal stimulation," Am J Physiol Heart Circ Physiol 282:H1102-H1110 (2002), describe the application of selective vagal stimulation by varying the nerve stimulation intensity, in order to achieve graded slowing of heart rate. This article is incorporated herein by reference.

A number of patents describe techniques for treating arrhythmias and/or ischemia by, at least in part, stimulating the vagus nerve. Arrhythmias in which the heart rate is too fast include fibrillation, flutter and tachycardia. Arrhythmia in which the heart rate is too slow is known as bradyarrhythmia. U.S. Pat. No. 5,700,282 to Zabara, which is incorporated herein by reference, describes techniques for stabilizing the heart rhythm of a patient by detecting arrhythmias and then electronically stimulating the vagus and cardiac sympathetic nerves of the patient. The stimulation of vagus efferents directly causes the heart rate to slow down, while the stimulation of cardiac sympathetic nerve efferents causes the heart rate to quicken.

European patent application EP 0 688 577 to Holmström et al., which is incorporated herein by reference, describes a device to treat atrial tachyarrhythmia by detecting arrhythmia and stimulating a parasympathetic nerve that innervates the heart, such as the vagus nerve.

U.S. Pat. Nos. 5,690,681 and 5,916,239 to Geddes et al., which are incorporated herein by reference, describe closed-loop, variable-frequency, vagal-stimulation apparatus for control of ventricular rate during atrial fibrillation. The apparatus stimulates the left vagus nerve, and automatically and continuously adjusts the vagal stimulation frequency as a function of the difference between actual and desired ventricular excitation rates. In an alternative embodiment, the apparatus automatically adjusts the vagal stimulation frequency as a function of the difference between ventricular excitation rate and arterial pulse rate in order to eliminate or minimize pulse deficit.

U.S. Pat. No. 5,522,854 to Ideker et al., which is incorporated herein by reference, describes techniques for preventing arrhythmia by detecting a high risk of arrhythmia and then stimulating afferent nerves to prevent the arrhythmia. By monitoring the sympathetic and parasympathetic nerve activity of a patient the risk of arrhythmia may be assessed.

U.S. Pat. No. 5,658,318 to Stroetmann et al., which is incorporated herein by reference, describes a device for detecting a state of imminent cardiac arrhythmia in response to activity in nerve signals conveying information from the autonomic nerve system to the heart. The device comprises a sensor adapted to be placed in an extracardiac position and to detect activity in at least one of the sympathetic and vagus nerves.

U.S. Pat. No. 5,578,061 to Stroetmann et al., which is incorporated herein by reference, describes a device for heart therapy that has a tacharrythmia detector unit, a control unit and a current generator. The current generator controlled by the control unit emits via an electrode system a first, pulsed current to a physiological representative of the parasympathetic nervous system in order to activate same in response to detection of an impending or established arrhythmia. The current generator is further caused by the control unit, in the event of tachyarrythmia detection to emit, via the electrode system, a second current to a physiological representative of the sympathetic nervous system in order to block same.

U.S. Pat. No. 7,050,846 to Sweeney et al., which is incorporated herein by reference, describes a cardiac rhythm management system that predicts when an arrhythmia will occur and in one embodiment invokes a therapy to prevent or reduce the consequences of the arrhythmia. A cardiac arrhythmia trigger/marker is detected from a patient, and based on the trigger/marker, the system estimates a probability of a cardiac arrhythmia occurring during a predetermined future time interval. The system provides a list of triggers/markers, for which detection values are recurrently obtained at various predetermined time intervals. Based on detection values and conditional probabilities associated with the triggers/markers, a probability estimate of a future arrhythmia is computed. An arrhythmia prevention therapy is selected and activated based on the probability estimate of the future arrhythmia.

U.S. Pat. No. 5,411,531 to Hill et al., which is incorporated herein by reference, describes a device for controlling the duration of A-V conduction intervals in a patient's heart. Stimulation of the AV nodal fat pad is employed to maintain the durations of the A-V conduction intervals within a desired interval range, which may vary as a function of sensed heart rate or other physiologic parameter. AV nodal fat pad stimulation may also be triggered in response to defined heart rhythms such as a rapid rate or the occurrence of PVC's, to terminate or prevent induction of arrhythmias.

U.S. Pat. No. 5,330,507 to Schwartz, which is incorporated herein by reference, describes techniques for stimulating the right or left vagus nerve with continuous and/or phasic electrical pulses, the latter in a specific relationship with the R-wave of the patient's electrogram. The automatic detection of the need for vagal stimulation is responsive to increases in the heart rate greater than a predetermined threshold, the occurrence of frequent or complex ventricular arrhythmias, and/or a change in the ST segment elevation greater than a predetermined or programmed threshold.

U.S. Pat. No. 6,292,695 to Webster, Jr. et al., which is incorporated herein by reference, describes a method for controlling cardiac fibrillation, tachycardia, or cardiac arrhythmia by the use of a catheter comprising a stimulating electrode, which is placed at an intravascular location. The electrode is connected to a stimulating means, and stimulation is applied across the wall of the vessel, transvascularly, to a sympathetic or parasympathetic nerve that innervates the heart at a strength sufficient to depolarize the nerve and effect the control of the heart.

U.S. Pat. No. 6,564,096 to Mest, which is incorporated herein by reference, describes a method for regulating the heart rate of a patient, comprising inserting into a blood vessel of the patient a catheter having an electrode assembly at its distal end. The electrode assembly comprises a generally circular main region that is generally transverse to the axis of the catheter and on which is mounted at least one electrode. The catheter is directed to an intravascular location wherein the at least one electrode on the electrode assembly is adjacent a selected cardiac sympathetic or parasympathetic nerve. The at least one electrode is stabilized at the intravascular location. A stimulus is delivered through the at least one electrode, the stimulus being selected to stimulate the adjacent sympathetic or parasympathetic nerve to thereby cause a regulation of the patient's heart rate.

U.S. Pat. No. 6,668,191 to Boveja, which is incorporated herein by reference, describes a system for neuromodulation adjunct (add-on) therapy for atrial fibrillation, refractory hypertension, and inappropriate sinus tachycardia, comprising an implantable lead-receiver and an external stimulator. Neuromodulation is performed using pulsed electrical stimulation. The external stimulator contains a power source, controlling circuitry, a primary coil, and predetermined programs. The primary coil of the external stimulator inductively transfers electrical signals to the implanted lead-receiver, which is also in electrical contact with a vagus nerve. The external stimulator emits electrical pulses to stimulate the vagus nerve according to a predetermined program. In a second mode of operation, an operator may manually override the predetermined sequence of stimulation. The external stimulator may also be equipped with a telecommunications module to control the predetermined programs remotely.

U.S. Pat. No. 6,934,583 to Weinberg et al., which is incorporated herein by reference, describes techniques for stimulating the right vagal nerve within a living body via positioning an electrode portion of a lead proximate to the portion of the vagus nerve where the right cardiac branch is located (e.g., near or within an azygos vein, or the superior vena cava near the opening of the azygos vein) and delivering an electrical signal to an electrode portion adapted to be implanted therein. Stimulation of the right vagus nerve and/or the cardiac branch thereof act to slow the atrial heart rate. Exemplary embodiments include deploying an expandable or self-oriented electrode (e.g., a basket, an electrode umbrella, and/or an electrode spiral electrode, electrode pairs, etc). Various dedicated and single-pass leads are disclosed, as well as, various electrodes, and stabilization means. The methods include preserving sinus rhythm, avoiding asystole, preserving A-V synchrony, automatically determining parameter combinations that achieve these features, and further (in one embodiment) automatically determining parameter combinations achieve these features and reduce current drain.

U.S. Pat. No. 6,134,470 to Hartlaub, which is incorporated herein by reference, describes an implantable anti-arrhythmia system which includes a spinal cord stimulator coupled to an implantable heart rhythm monitor. The monitor is adapted to detect the occurrence of tachyarrhythmias or of precursors thereto and, in response, trigger the operation of the spinal cord stimulator in order to prevent occurrences of tachyarrhythmias and/or as a stand-alone therapy for termination of tachyarrhythmias and/or to reduce the level of aggressiveness required of an additional therapy such as antitachycardia pacing, cardioversion or defibrillation.

Schaldach M, in "New concepts in electrotherapy of the heart," *Electrotherapy of the heart*, Springer Verlag Heidelberg, pp. 210-214 (1992), which is incorporated herein by reference, writes that "a general concept of electrical treatment of arrhythmia becomes possible if the neural factors in the *arrhythmogenesis* are considered. With the powerful tool of monitoring the sympathetic tone by intraventricular impedance measurements, the VIP that was introduced for the restoration of chronotropy will serve as a sensor of the increased neural activity of an impending arrhythmia, therefore making it possible to prevent tachycardia" (p. 210, emphasis in the original).

The following patents, patent application publications, articles, and book, all of which are incorporated herein by reference, may be of interest:

US Patent Publication 2003/0229380 to Adams et al.
U.S. Pat. No. 5,203,326 to Collins
U.S. Pat. No. 6,511,500 to Rahme
U.S. Pat. No. 5,199,428 to Obel et al.
U.S. Pat. No. 5,334,221 to Bardy
U.S. Pat. No. 5,356,425 to Bardy et al.
U.S. Pat. No. 6,434,424 to Igel et al.
US Patent Application Publication 2002/0120304 to Mest
U.S. Pat. Nos. 6,006,134 and 6,266,564 to Hill et al.
PCT Publication WO 02/085448 to Foreman et al.
U.S. Pat. No. 5,243,980 to Mehra
U.S. Pat. No. 6,473,644 to Terry, Jr. et al.
U.S. Pat. No. 6,622,041 to Terry, Jr. et al.
US Patent Publication 2003/0045909 to Gross et al.
US Patent Publication 2003/0050677 to Gross et al.
U.S. Pat. No. 4,608,985 to Crish et al.
U.S. Pat. No. 4,649,936 to Ungar et al.
PCT Patent Publication WO 01/10375 to Felsen et al.
U.S. Pat. No. 5,755,750 to Petruska et al.
U.S. Pat. No. 5,231,988 to Wernicke et al.
U.S. Pat. No. 7,142,917 to Fukui Youhua Z et al., "Optimal vertricular rate slowing during atrial fibrillation by feedback AV nodal-selective vagal stimulation," Am J Physiol Heart Circ Physiol 282:H1102-H1110 (2002) Moreira et al., entitled, "Chronic rapid atrial pacing to maintain atrial fibrillation: Use to permit control of ventricular rate in order to treat tachycardia induced cardiomyopathy," Pacing Clin Electrophysiol, 12(5):761-775 (May 1989)

Preston et al., entitled, "Permanent rapid atrial pacing to control supraventricular tachycardia," Pacing Clin Electrophysiol, 2(3):331-334 (May 1979)

Levy M N et al., in "Parasympathetic Control of the Heart," Nervous Control of Vascular Function, Randall W C ed., Oxford University Press (1984)

Levy M N et al. ed., Vagal Control of the Heart: Experimental Basis and Clinical Implications (The Bakken Research Center Series Volume 7), Futura Publishing Company, Inc., Armonk, N.Y. (1993)

Randall W C ed., Neural Regulation of the Heart, Oxford University Press (1977), particularly pages 100-106.

Armour J A et al. eds., Neurocardiology, Oxford University Press (1994)

Perez M G et al., "Effect of stimulating non-myelinated vagal axon on atrio-ventricular conduction and left ventricular function in anaesthetized rabbits," Auton Neurosco 86 (2001)

Jones, J F X et al., "Heart rate responses to selective stimulation of cardiac vagal C fibres in anaesthetized cats, rats and rabbits," J Physiol 489 (Pt 1):203-14 (1995)

Wallick D W et al., "Effects of ouabain and vagal stimulation on heart rate in the dog," Cardiovasc. Res., 18(2):75-9 (1984)

Wallick D W et al., "Effects of repetitive bursts of vagal activity on atrioventricular junctional rate in dogs," Am J Physiol 237(3):H275-81 (1979)

Wallick D W et al., "Selective AV nodal vagal stimulation improves hemodynamics during acute atrial fibrillation in dogs," Am J Physiol Heart Circ Physiol 281: H1490-H1497 (2001)

Martin P J et al., "Phasic effects of repetitive vagal stimulation on atrial contraction," Circ. Res. 52(6):657-63 (1983)

Fuster V and Ryden L E et al., "ACC/AHA/ESC Practice Guidelines—Executive Summary," J Am Coll Cardiol 38(4): 1231-65 (2001)

Fuster V and Ryden L E et al., "ACC/AHA/ESC Practice Guidelines—Full Text," J Am Coll Cardiol 38(4):1266i-12661xx (2001)

Morady F et al., "Effects of resting vagal tone on accessory atrioventricular connections," Circulation 81(1):86-90 (1990)

Waninger M S et al., "Electrophysiological control of ventricular rate during atrial fibrillation," PACE 23:1239-1244 (2000)

Wijffels M C et al., "Electrical remodeling due to atrial fibrillation in chronically instrumented conscious goats: roles of neurohumoral changes, ischemia, atrial stretch, and high rate of electrical activation," Circulation 96(10):3710-20 (1997)

Wijffels M C et al., "Atrial fibrillation begets atrial fibrillation," Circulation 92:1954-1968 (1995)

Goldberger A L et al., "Vagally-mediated atrial fibrillation in dogs: conversion with bretylium tosylate," Int J Cardiol 13(1):47-55 (1986)

Takei M et al., "Vagal stimulation prior to atrial rapid pacing protects the atrium from electrical remodeling in anesthetized dogs," Jpn Circ J 65(12):1077-81 (2001)

Friedrichs G S, "Experimental models of atrial fibrillation/flutter," J Pharmacological and Toxicological Methods 43:117-123 (2000)

Hayashi H et al., "Different effects of class Ic and III antiarrhythmic drugs on vagotonic atrial fibrillation in the canine heart," Journal of Cardiovascular Pharmacology 31:101-107 (1998)

Morillo C A et al., "Chronic rapid atrial pacing. Structural, functional, and electrophysiological characteristics of a new model of sustained atrial fibrillation," Circulation 91:1588-1595 (1995)

Lew S J et al., "Stroke prevention in elderly patients with atrial fibrillation," Singapore Med J 43(4):198-201 (2002)

Higgins C B, "Parasympathetic control of the heart," Pharmacol. Rev. 25:120-155 (1973)

Hunt R, "Experiments on the relations of the inhibitory to the accelerator nerves of the heart," J. Exptl. Med. 2:151-179 (1897)

Billette J et al., "Roles of the AV junction in determining the ventricular response to atrial fibrillation," Can J Physiol Pharamacol 53(4)575-85 (1975)

Stramba-Badiale M et al., "Sympathetic-Parasympathetic Interaction and Accentuated Antagonism in Conscious Dogs," American Journal of Physiology 260 (2Pt2):H335-340 (1991)

Garrigue S et al., "Post-ganglionic vagal stimulation of the atrioventricular node reduces ventricular rate during atrial fibrillation," PACE 21(4), 878 (Part II) (1998)

Kwan H et al., "Cardiovascular adverse drug reactions during initiation of antiarrhythmic therapy for atrial fibrillation," Can J Hosp Pharm 54:10-14 (2001)

Jidéus L, "Atrial fibrillation after coronary artery bypass surgery: A study of causes and risk factors," Acta Universitatis Upsaliensis, Uppsala, Sweden (2001)

Borovikova L V et al., "Vagus nerve stimulation attenuates the systemic inflammatory response to endotoxin," Nature 405(6785):458-62 (2000)

Wang H et al., "Nicotinic acetylcholine receptor alpha-7 subunit is an essential regulator of inflammation," Nature 421:384-388 (2003)

Vanoli E et al., "Vagal stimulation and prevention of sudden death in conscious dogs with a healed myocardial infarction," Circ Res 68(5):1471-81 (1991)

De Ferrari G M, "Vagal reflexes and survival during acute myocardial ischemia in conscious dogs with healed myocardial infarction," Am J Physiol 261(1 Pt 2):H63-9 (1991)

Li D et al., "Promotion of Atrial Fibrillation by Heart Failure in Dogs: Atrial Remodeling of a Different Sort," Circulation 100(1):87-95 (1999)

Feliciano L et al., "Vagal nerve stimulation during muscarinic and beta-adrenergic blockade causes significant coronary artery dilation," Cardiovasc Res 40(1):45-55 (1998)

Ungar I J et al., "Generation of unidirectionally propagating action potentials using a monopolar electrode cuff," Annals of Biomedical Engineering, 14:437-450 (1986)

Sweeney J D et al., "An asymmetric two electrode cuff for generation of unidirectionally propagated action potentials," IEEE Transactions on Biomedical Engineering, vol. BME-33 (6) (1986)

Sweeney J D et al., "A nerve cuff technique for selective excitation of peripheral nerve trunk regions," IEEE Transactions on Biomedical Engineering, 37(7) (1990)

Naples G G et al., "A spiral nerve cuff electrode for peripheral nerve stimulation," by IEEE Transactions on Biomedical Engineering, 35(11) (1988)

van den Honert C et al., "Generation of unidirectionally propagated action potentials in a peripheral nerve by brief stimuli," Science, 206:1311-1312 (1979)

van den Honert C et al., "A technique for collision block of peripheral nerve: Single stimulus analysis," MP-11, IEEE Trans. Biomed. Eng. 28:373-378 (1981)

van den Honert C et al., "A technique for collision block of peripheral nerve: Frequency dependence," MP-12, IEEE Trans. Biomed. Eng. 28:379-382 (1981)

Rijkhoff N J et al., "Acute animal studies on the use of anodal block to reduce urethral resistance in sacral root stimulation," IEEE Transactions on Rehabilitation Engineering, 2(2):92 (1994)

Mushahwar V K et al., "Muscle recruitment through electrical stimulation of the lumbo-sacral spinal cord," IEEE Trans Rehabil Eng, 8(1):22-9 (2000)

Deurloo K E et al., "Transverse tripolar stimulation of peripheral nerve: a modelling study of spatial selectivity," Med Biol Eng Comput, 36(1):66-74 (1998)

Tarver W B et al., "Clinical experience with a helical bipolar stimulating lead," Pace, Vol. 15, October, Part II (1992)

Manfredi M, "Differential block of conduction of larger fibers in peripheral nerve by direct current," Arch. Ital. Biol., 108:52-71 (1970)

In physiological muscle contraction, nerve fibers are recruited in the order of increasing size, from smaller-diameter fibers to progressively larger-diameter fibers. In contrast, artificial electrical stimulation of nerves using standard techniques recruits fibers in a larger- to smaller-diameter order, because larger-diameter fibers have a lower excitation threshold. This unnatural recruitment order causes muscle fatigue and poor force gradation. Techniques have been explored to mimic the natural order of recruitment when performing artificial stimulation of nerves to stimulate muscles.

Fitzpatrick et al., in "A nerve cuff design for the selective activation and blocking of myelinated nerve fibers," Ann. Conf. of the IEEE Eng. in Medicine and Biology Soc, 13(2), 906 (1991), which is incorporated herein by reference, describe a tripolar electrode used for muscle control. The electrode includes a central cathode flanked on its opposite sides by two anodes. The central cathode generates action potentials in the motor nerve fiber by cathodic stimulation. One of the anodes produces a complete anodal block in one direction so that the action potential produced by the cathode is unidirectional. The other anode produces a selective anodal block to permit passage of the action potential in the opposite direction through selected motor nerve fibers to produce the desired muscle stimulation or suppression.

The following articles, which are incorporated herein by reference, may be of interest:

Rijkhoff N J et al., "Orderly recruitment of motoneurons in an acute rabbit model," Ann. Conf. of the IEEE Eng., Medicine and Biology Soc., 20(5):2564 (1998)

Rijkhoff N J et al., "Selective stimulation of small diameter nerve fibers in a mixed bundle," Proceedings of the Annual Project Meeting Sensations/Neuros and Mid-Term Review Meeting on the TMR-Network Neuros, Apr. 21-23, 1999, pp. 20-21 (1999)

Baratta R et al., "Orderly stimulation of skeletal muscle motor units with tripolar nerve cuff electrode," IEEE Transactions on Biomedical Engineering, 36(8):836-43 (1989)

The following articles, which are incorporated herein by reference, describe techniques using point electrodes to selectively excite peripheral nerve fibers:

Grill W M et al., "Inversion of the current-distance relationship by transient depolarization," IEEE Trans Biomed Eng, 44(1):1-9 (1997)

Goodall E V et al., "Position-selective activation of peripheral nerve fibers with a cuff electrode," IEEE Trans Biomed Eng, 43(8):851-6 (1996)

Veraart C et al., "Selective control of muscle activation with a multipolar nerve cuff electrode," IEEE Trans Biomed Eng, 40(7):640-53 (1993)

As defined by Rattay, in the article, "Analysis of models for extracellular fiber stimulation," IEEE Transactions on Biomedical Engineering, Vol. 36, no. 2, p. 676, 1989, which is incorporated herein by reference, the activation function is the second spatial derivative of the electric potential along an axon. In the region where the activation function is positive, the axon depolarizes, and in the region where the activation function is negative, the axon hyperpolarizes. If the activation function is sufficiently positive, then the depolarization will cause the axon to generate an action potential; similarly, if the activation function is sufficiently negative, then local blocking of action potentials transmission occurs. The activation function depends on the current applied, as well as the geometry of the electrodes and of the axon.

The following patents and patent application publications, all of which are assigned to the assignee of the present application and are incorporated herein by reference, may be of interest:

US Patent Application Publication 2003/0050677
US Patent Application Publication 2003/0045909
PCT Publication WO 03/018113
U.S. Pat. No. 6,684,105
US Patent Application Publication 2004/0254612
PCT Publication WO 03/099373
PCT Publication WO 03/099377
US Patent Application Publication 2004/0193231
PCT Publication WO 04/103455
PCT Publication WO 04/110550
US Patent Application Publication 2005/0065553
PCT Publication WO 04/110549
US Patent Application Publication 2006/0136024
US Patent Application Publication 2005/0197675
US Patent Application Publication 2005/0267542
US Patent Application Publication 2006/0106441
US Patent Application Publication 2006/0167501
US Patent Application Publication 2006/0206155
US Patent Application Publication 2005/0149154
US Patent Application Publication 2006/0100668

SUMMARY OF THE INVENTION

In some embodiments of the present invention, a method for treating a subject at risk of suffering from atrial fibrillation (AF) comprises reducing the risk of an occurrence of an episode of the AF by applying an electrical current to a vagus nerve or other parasympathetic tissue that innervates the heart of the subject. Apparatus is provided for applying the electrical current, comprising an electrode device and a control unit, which is configured to drive the electrode device to apply the current.

Typically, the control unit is configured to apply the current on a chronic, long-term basis, even when the subject is not currently experiencing an episode of the AF, and even in the absence of a prediction of an imminent episode of the AF. The current is thus typically applied during normal sinus rhythm (NSR). For some applications, the control unit applies the current not responsively to any physiological parameters sensed by the control unit or a sensor coupled to the control unit. For some applications, the control unit applies the current not responsively to any measure of heart rate of the subject (which may be expressed as a heart rate or interval, e.g., an R-R interval) determined by the control unit. For these application, the control unit does not configure any parameters of the applied current responsively to any measure of the heart rate, including any timing parameters of the current application.

The control unit typically does not configure the current to achieve regulation of a heart rate of the subject, such as to achieve a target heart rate or range. For some applications, the current is configured to minimize an effect of the applying of the current on a heart rate of the subject.

For some applications, the control unit configures the current to delay electrical remodeling of an atrium of the subject, to reduce mechanical stress of a heart of the subject, and/or to induce rhythmic vagal activity.

In some embodiments of the present invention, upon sensing an occurrence of an episode of the AF, the control unit reduces a strength of the current, e.g., withholds applying the current, typically during a strength reduction period having a duration of at least one minute, e.g., at least 5 minutes, at least 10 minutes, at least 20 minutes, or at least one hour. The inventors believe that application of the current sometimes prolongs episodes of AF, so reducing the strength of or withholding the current generally allows episodes to resolve more quickly than they would during application of the current at full strength. Similarly, for some applications, upon predicting an imminent episode of the AF, the control unit reduces the strength of the current, e.g., withholds applying the current. For some applications, upon conclusion of the strength reduction period, the control unit configures the current to reduce a heart rate of the subject if the episode of AF has not terminated, and the subject has an elevated heart rate.

In some embodiments of the present invention, the control unit applies the current in a series of bursts, each of which bursts includes at least one pulse. For some applications, the control unit synchronizes at least a portion of the bursts with a feature of a cardiac cycle of the subject, such as a P-wave or R-wave. Synchronization with the P-wave has the effect of automatically withholding stimulation during AF, because no P-wave is present during AF.

In some embodiments of the present invention, the subject is determined to be at risk of suffering from AF by identifying that the subject suffers from at least one of the following conditions:

paroxysmal AF;
self-terminating AF episodes;
an enlarged atrium;
multiple atrial premature beats (APBs);
mitral stenosis;
heart failure;
thyrotoxicosis;
hypertension; and
atrial flutter.

Alternatively or additionally, the subject is determined to be at risk of suffering from AF by identifying that the subject has undergone an interventional heart procedure, such as coronary bypass surgery or valve replacement surgery.

For some applications, this determination is made after the subject has suffered from at least one episode of the AF, while for other applications, the determination is made prior to the subject suffering from any known episodes of the AF.

In some embodiments of the present invention, the control unit drives the electrode device to (a) apply signals to induce the propagation of efferent action potentials towards the heart, and (b) suppress artificially-induced afferent action potentials towards the brain, in order to minimize any unintended side effect of the signal application. When inducing efferent action potentials towards the heart, the control unit typically drives the electrode device to selectively recruit nerve fibers beginning with smaller-diameter fibers, and to recruit progressively larger-diameter fibers as the desired stimulation level increases. Typically, in order to achieve this smaller-to-larger diameter fiber recruitment order, the control unit stimulates fibers essentially of all diameters using cathodic current from a central cathode, while simultaneously inhibiting fibers in a larger-to-smaller diameter order using anodal current ("efferent anodal current") from a set of one or more anodes placed between the central cathode and the edge of the electrode device closer to the heart ("the efferent anode set"). Thus, for example, if a small anodal current is applied, then action potentials induced by the cathodic current in the larger diameter fibers are inhibited (because the larger diameter fibers are sensitive to even a small anodal current), while action potentials induced by the cathodic current in smaller fibers are allowed to propagate towards the heart. The amount of parasympathetic stimulation delivered to the heart may generally be increased by decreasing the number of fibers affected by the efferent anodal current, in a smaller-to-larger diameter order, e.g., by decreasing the amplitude or frequency of the efferent anodal current applied to the nerve. Alternatively, the cathodic current is increased in order to increase the parasympathetic stimulation.

The control unit typically suppresses afferent action potentials induced by the cathodic current by inhibiting essentially all or a large fraction of fibers using anodal current ("afferent anodal current") from a second set of one or more anodes (the "afferent anode set"). The afferent anode set is typically placed between the central cathode and the edge of the electrode device closer to the brain (the "afferent edge"), to block a large fraction of fibers from conveying signals in the direction of the brain during application of the afferent anodal current.

In some embodiments of the present invention, the current is applied in a series of pulses. The application of the series of pulses in each cardiac cycle typically commences after a variable delay after a detected R-wave, P-wave, or other feature of an ECG. For some applications, other parameters of the applied series of pulses are also varied in real time. Such other parameters include amplitude, number of pulses per trigger (PPT), pulse duration, and pulse repetition interval (i.e., the interval between the leading edges of two consecutive pulses). For some applications, the delay and/or one or more of the other parameters are calculated in real time using a function, the inputs of which include one or more pre-programmed but updateable constants and one or more sensed parameters, such as the R-R interval between cardiac cycles and/or the P-R interval. Alternatively or additionally, a lookup table of parameters, such as delays and/or other parameters, is used to determine in real time the appropriate parameters for each application of pulses, based on the one or more sensed parameters, and/or based on a predetermined sequence stored in the lookup table.

In some embodiments of the present invention, the electrical current described herein is applied to a site selected from the group consisting of: a vagus nerve, an epicardial fat pad, a sinoatrial (SA) node fat pad, a pulmonary vein, a carotid artery, a carotid sinus, a coronary sinus, a vena cava vein, a jugular vein, an azygos vein, an innominate vein, and a subclavian vein, and the current is configured to stimulate autonomic nervous tissue in the site. Alternatively or additionally, the site is selected from the group consisting of: a right ventricle and a right atrium. "Vagus nerve," and derivatives thereof, as used in the present application including the claims, is to be understood to include portions of the left vagus nerve, the right vagus nerve, and branches of the vagus nerve such as the cervical or thoracic vagus nerve, superior cardiac branch, and inferior cardiac branch.

There is therefore provided, in accordance with an embodiment of the present invention, a method including:

identifying that a subject is at risk of suffering from atrial fibrillation (AF); and responsively to the identifying, reducing a risk of an occurrence of an episode of the AF by:

applying an electrical current to a site of the subject selected from the group consisting of: a vagus nerve, a sinoatrial (SA) node fat pad, a pulmonary vein, a carotid artery, a carotid sinus, a coronary sinus, a vena cava vein, a jugular vein, an azygos vein, an innominate vein, and a subclavian vein, and configuring the current to stimulate autonomic nervous tissue in the site.

In an embodiment, applying the current includes applying the current even in the absence of a prediction of an imminent episode of the AF. In an embodiment, applying the current includes applying the current in the absence of a prediction of an imminent episode of the AF. In an embodiment, applying the current includes detecting normal sinus rhythm (NSR) of the subject, and applying the current during the detected NSR.

In an embodiment, applying the current does not include configuring the current to achieve a target heart rate or a target heart rate range of the subject.

For some applications, identifying that the subject is at risk includes identifying that the subject suffers from a condition selected from the group consisting of: paroxysmal AF, and self-terminating AF episodes. Alternatively or additionally, identifying that the subject is at risk includes identifying that the subject suffers from at least one condition selected from the group consisting of: an enlarged atrium, multiple atrial premature beats (APBs), mitral stenosis, heart failure, thyrotoxicosis, hypertension, and atrial flutter.

For some applications, identifying includes identifying, after the subject has suffered from at least one episode of the AF, that the subject is at risk. Alternatively, identifying includes identifying, prior to the subject suffering from any known episodes of the AF, that the subject is at risk. Typically, identifying includes identifying by a medical professional that the subject is at risk.

For some applications, applying the current includes configuring the current to delay electrical remodeling of an atrium of the subject, to reduce mechanical stress of a heart of the subject, and/or to induce rhythmic vagal activity.

For some applications, applying the current includes commencing applying at least 24 hours after the identifying.

For some applications, applying the current includes:

applying, during stimulation periods that alternate with rest periods, the current during "on" periods that alternate with low stimulation periods, the "on" periods having on average an "on" duration equal to at least 1 second, and the low stimulation periods having on average a low stimulation duration equal to at least 50% of the "on" duration;

setting the current applied on average during the low stimulation periods to be less than 20% of the current applied on average during the "on" periods;

setting the current applied on average during the rest periods to be less than 20% of the current applied on average during the "on" periods; and setting the rest periods to have on average a rest period duration equal to at least a cycle duration that equals a duration of a single "on" period plus a duration of a single low stimulation period, and the stimulation periods to have on average a stimulation period duration equal to at least five times the rest period duration.

In an embodiment, applying the current includes:
sensing the occurrence of the episode of the AF; and
responsively to the sensing, configuring the current to reduce a heart rate of the subject.

In an embodiment, applying the current includes applying the current even during the occurrence of the episode of the AF, without configuring the current to resolve the episode.

For some applications, the site includes the sinoatrial (SA) node fat pad, and applying the current includes applying the current to the SA node fat pad.

In an embodiment, applying the current includes detecting whether applying the current causes one or more cardiac contractions, and responsively to finding that applying the current causes the contractions, reducing a strength of the current to a level insufficient to cause the contractions.

In an embodiment, applying the current includes applying the current at least once during each of seven consecutive 48-hour periods. For some applications, applying the current at least once during each of the seven consecutive 48-hour periods includes applying the current at least once during each of 14 consecutive 24-hour periods. For some applications, applying the current at least once during each of the 14 consecutive 24-hour periods includes applying the current at least once during each of 28 consecutive 12-hour periods. For some applications, applying the current includes applying the current in a plurality of pulses, and applying the current at least once during each of the 14 consecutive 24-hour periods includes applying the current in at least 100 of the pulses during each of the 14 consecutive 24-hour periods.

In an embodiment, the site includes the vagus nerve, and applying the current includes applying the current to the vagus nerve. In an embodiment, applying the current includes configuring the current to induce propagation of efferent action potentials traveling towards a heart of the subject, and to suppress artificially-induced afferent action potentials traveling towards a brain of the subject. For some applications, the vagus nerve includes a right vagus nerve, and applying the current includes applying the current to the right vagus nerve.

In an embodiment, applying the current includes configuring the current so as to minimize an effect of the applying of the current on a heart rate of the subject. For some applications, applying the current includes:

setting a threshold heart rate;
sensing the heart rate of the subject;
comparing the sensed heart rate with the threshold heart rate; and
applying the current upon finding that the sensed heart rate is less than the threshold heart rate.

In an embodiment, applying the current includes:
applying the current at a first strength on average;
sensing the occurrence of the episode of the AF; and
responsively to the sensing, applying the current at a second strength on average during a strength reduction period having a duration of at least one minute, which second strength is less than the first strength.

For some applications, applying the current at the second strength includes withholding applying the current. For some applications, applying the current includes, upon a conclusion of the strength reduction period, configuring the current to reduce a heart rate of the subject, upon sensing that the episode of the AF has not terminated and that the subject has an elevated heart rate.

In an embodiment, applying the current includes:
applying the current at a first strength on average;
predicting an imminent episode of the AF; and
responsively to the predicting, applying the current at a second strength on average during a strength reduction period having a duration of at least one minute, which second strength is less than the first strength.

For some applications, applying the current at the second strength includes withholding applying the current.

In an embodiment, identifying includes identifying that the subject is at risk because the subject has undergone an interventional heart procedure. For some applications, the heart procedure includes coronary bypass surgery, and identifying includes identifying that the subject is at risk because the subject has undergone the coronary bypass surgery. For some applications, the heart procedure includes valve replacement surgery, and identifying includes identifying that the subject is at risk because the subject has undergone the valve replacement surgery.

In an embodiment, applying the current includes applying the current in a series of bursts, each of which bursts includes one or more pulses. For some applications, the series of bursts includes at least first and second bursts, the first burst including a plurality of the pulses, and the second burst including at least one of the pulses, and applying the current includes setting (a) a pulse repetition interval (PRI) of the first burst to be on average at least 20 ms, (b) an interburst interval between initiation of the first burst and initiation of the second burst to be less than 10 seconds, (c) an interburst gap between a conclusion of the first burst and the initiation of the second burst to have a duration greater than the average PRI, and (d) a burst duration of the first burst to be less than a percentage of the interburst interval, the percentage being less than 67%.

For some applications, applying the current includes:
applying, during "on" periods that alternate with low stimulation periods, at least one of the "on" periods having an "on" duration of at least three seconds, and including at least three of the bursts, and at least one of the low stimulation periods immediately following the at least one of the "on" periods having a low stimulation duration equal to at least 50% of the "on" duration;

setting the current applied on average during the low stimulation periods to be less than 20% of the current applied on average during the "on" periods; and during at least one transitional period of the at least one of the "on" periods, ramping a number of pulses per burst, the at least one transitional period selected from the group consisting of: a commencement of the at least one of the "on" periods, and a conclusion of the at least one of the "on" periods.

For some applications, applying the current includes synchronizing at least a portion of the bursts with a feature of a cardiac cycle of the subject. For example, the feature of the cardiac cycle may include a P-wave, and applying the current includes synchronizing the at least a portion of the bursts with the P-wave. Alternatively, the feature of the cardiac cycle may include a R-wave, and applying the current includes synchronizing the at least a portion of the bursts with the R-wave.

In an embodiment, applying the current includes: coupling an electrode device to the site; and driving, by a control unit, the electrode device to apply the current. In an embodiment, reducing the risk includes reducing the risk in the absence of a determination by any device directly or indirectly coupled to the control unit that the subject is at risk of suffering from the AF. For some applications, driving includes driving the electrode device to apply the current not responsively to any physiological parameters sensed by any device directly or indirectly coupled to the control unit. For some applications, driving includes driving the electrode device to apply the current not responsively to any measure of a heart rate of the subject determined by the control unit.

There is further provided, in accordance with an embodiment of the present invention, apparatus including:

an electrode device, configured to be coupled to a site of the subject at risk of suffering from atrial fibrillation (AF), the site selected from the group consisting of: a vagus nerve, a sinoatrial (SA) node fat pad, a pulmonary vein, a carotid artery, a carotid sinus, a coronary sinus, a vena cava vein, a jugular vein, an azygos vein, an innominate vein, and a subclavian vein; and a control unit, configured to reduce a risk of an occurrence of an episode of the AF by:

driving the electrode device to apply an electrical current to the site, and configuring the current to stimulate autonomic nervous tissue in the site.

There is still further provided, in accordance with an embodiment of the present invention, a method including:

identifying that a subject is at risk of suffering from atrial fibrillation (AF);

responsively to the identifying, delaying electrical remodeling of an atrium of the subject that may be caused by the AF, by:

applying an electrical current to a site of the subject containing parasympathetic nervous tissue, and configuring the current to stimulate the nervous tissue in the site.

In an embodiment, the site is selected from the group consisting of: a vagus nerve, an epicardial fat pad, a sinoatrial (SA) node fat pad, a pulmonary vein, a carotid artery, a carotid sinus, a coronary sinus, a vena cava vein, a jugular vein, an azygos vein, an innominate vein, and a subclavian vein, and applying the current includes applying the current to the selected site.

In an embodiment, the site is selected from the group consisting of: the vagus nerve, the epicardial fat pad, the pulmonary vein, the carotid artery, the carotid sinus, the vena cava vein, and the jugular vein, and applying the current includes applying the current to the selected site.

For some applications, delaying the electrical remodeling includes preventing the electrical remodeling of the atrium.

In an embodiment, applying the current includes applying the current even in the absence of a prediction of an imminent episode of the AF. In an embodiment, applying the current includes applying the current in the absence of a prediction of an imminent episode of the AF. In an embodiment, applying the current includes detecting normal sinus rhythm (NSR) of the subject, and applying the current during the detected NSR.

In an embodiment, applying the current does not include configuring the current to achieve a target heart rate or a target heart rate range of the subject.

For some applications, the method includes identifying that the subject suffers from heart failure (HF), and delaying includes, delaying, responsively to the identifying that the subject is at risk of suffering from the AF and that the subject suffers from the HF, the electrical remodeling that may be caused by the AF or by the HF.

Typically, identifying includes identifying by a medical professional that the subject is at risk.

For some applications, delaying includes delaying by administering a drug for treating the AF, responsively to the identifying.

In an embodiment, applying the current includes detecting an episode of the AF, and applying the current responsively to the detecting.

In an embodiment, applying the current includes applying the current not responsively to detecting an episode of the AF.

For some applications, applying the current includes commencing applying at least 24 hours after the identifying.

For some applications, identifying that the subject is at risk includes identifying that the subject suffers from a condition selected from the group consisting of: paroxysmal AF, and self-terminating AF episodes. Alternatively or additionally, identifying that the subject is at risk includes identifying that the subject suffers from at least one condition selected from the group consisting of: an enlarged atrium, multiple atrial premature beats (APBs), mitral stenosis, heart failure, thyrotoxicosis, hypertension, and atrial flutter.

For some applications, identifying includes identifying, after the subject has suffered from at least one episode of the AF, that the subject is at risk. Alternatively, identifying includes identifying, prior to the subject suffering from any known episodes of the AF, that the subject is at risk.

For some applications, applying the current includes configuring the current to reduce mechanical stress of a heart of the subject. For some applications, applying the current includes configuring the current to induce rhythmic vagal activity.

For some applications, applying the current includes:

applying, during stimulation periods that alternate with rest periods, the current during "on" periods that alternate with low stimulation periods, the "on" periods having on average an "on" duration equal to at least 1 second, and the low stimulation periods having on average a low stimulation duration equal to at least 50% of the "on" duration;

setting the current applied on average during the low stimulation periods to be less than 20% of the current applied on average during the "on" periods;

setting the current applied on average during the rest periods to be less than 20% of the current applied on average during the "on" periods; and setting the rest periods to have on average a rest period duration equal to at least a cycle duration that equals a duration of a single "on" period plus a duration of a single low stimulation period, and the stimulation periods to have on average a stimulation period duration equal to at least five times the rest period duration.

For some applications, the site includes a sinoatrial (SA) node fat pad, and applying the current includes applying the current to the SA node fat pad.

For some applications, applying the current includes applying the current even during an episode of the AF, without configuring the current to resolve the episode.

In an embodiment, the site includes the vagus nerve, and applying the current includes applying the current to the vagus nerve. In an embodiment, applying the current includes configuring the current to induce propagation of efferent action potentials traveling towards a heart of the subject, and suppress artificially-induced afferent action potentials traveling towards a brain of the subject. For some applications, the vagus nerve includes a right vagus nerve, and applying the current includes applying the current to the right vagus nerve.

In an embodiment, applying the current includes configuring the current so as to minimize an effect of the applying of the current on a heart rate of the subject. For some applications, applying the current includes:

setting a threshold heart rate;
sensing the heart rate of the subject;
comparing the sensed heart rate with the threshold heart rate; and
applying the current upon finding that the sensed heart rate is less than the threshold heart rate.

In an embodiment, applying the current includes applying the current at least once during each of seven consecutive 48-hour periods. For some applications, applying the current at least once during each of the seven consecutive 48-hour periods includes applying the current at least once during each of 14 consecutive 24-hour periods. For some applications, applying the current at least once during each of the 14 consecutive 24-hour periods includes applying the current at least once during each of 28 consecutive 12-hour periods. For some applications, applying the current includes applying the current in a plurality of pulses, and applying the current at least once during each of the 14 consecutive 24-hour periods includes applying the current in at least 100 of the pulses during each of the 14 consecutive 24-hour periods.

In an embodiment, applying the current includes applying the current during an episode of the AF, and does not include configuring the current to resolve the episode. For some applications, applying the current during the episode includes applying the current during the episode and during at least one period not during the episode. For some applications, applying the current during the episode includes detecting the episode, and applying the current responsively to the detecting.

In an embodiment, applying the current includes:
applying the current at a first strength on average;
sensing an occurrence of an episode of the AF; and
responsively to the sensing, applying the current at a second strength on average during a strength reduction period having a duration of at least one minute, which second strength is less than the first strength.

For some applications, applying the current at the second strength includes withholding applying the current. For some applications, applying the current includes, upon a conclusion of the strength reduction period, configuring the current to reduce a heart rate of the subject, upon sensing that the episode of the AF has not terminated and that the subject has an elevated heart rate.

In an embodiment, applying the current includes:
applying the current at a first strength on average;
predicting an imminent episode of the AF; and
responsively to the predicting, applying the current at a second strength on average during a strength reduction period having a duration of at least one minute, which second strength is less than the first strength.

For some applications, applying the current at the second strength includes withholding applying the current.

In an embodiment, identifying includes identifying that the subject is at risk because the subject has undergone an interventional heart procedure. For some applications, the heart procedure includes coronary bypass surgery, and identifying includes identifying that the subject is at risk because the subject has undergone the coronary bypass surgery. For some applications, the heart procedure includes valve replacement surgery, and identifying includes identifying that the subject is at risk because the subject has undergone the valve replacement surgery.

In an embodiment, applying the current includes applying the current in a series of bursts, each of which bursts includes one or more pulses. For some applications, the series of bursts includes at least first and second bursts, the first burst including a plurality of the pulses, and the second burst including at least one of the pulses, and applying the current includes setting (a) a pulse repetition interval (PRI) of the first burst to be on average at least 20 ms, (b) an interburst interval between initiation of the first burst and initiation of the second burst to be less than 10 seconds, (c) an interburst gap between a conclusion of the first burst and the initiation of the second burst to have a duration greater than the average PRI, and (d) a burst duration of the first burst to be less than a percentage of the interburst interval, the percentage being less than 67%.

For some applications, applying the current includes:
applying, during "on" periods that alternate with low stimulation periods, at least one of the "on" periods having an "on" duration of at least three seconds, and including at least three of the bursts, and at least one of the low stimulation periods immediately following the at least one of the "on" periods having a low stimulation duration equal to at least 50% of the "on" duration;

setting the current applied on average during the low stimulation periods to be less than 20% of the current applied on average during the "on" periods; and during at least one transitional period of the at least one of the "on" periods, ramping a number of pulses per burst, the at least one transitional period selected from the group consisting of: a commencement of the at least one of the "on" periods, and a conclusion of the at least one of the "on" periods.

For some applications, applying the current includes synchronizing at least a portion of the bursts with a feature of a cardiac cycle of the subject. For example, the feature of the cardiac cycle may include a P-wave, and applying the current includes synchronizing the at least a portion of the bursts with the P-wave. Alternatively, the feature of the cardiac cycle may include a R-wave, and applying the current includes synchronizing the at least a portion of the bursts with the R-wave.

In an embodiment, applying the current includes: coupling an electrode device to the site; and driving, by a control unit, the electrode device to apply the current. In an embodiment, reducing the risk includes reducing the risk in the absence of a determination by any device directly or indirectly coupled to the control unit that the subject is at risk of suffering from the AF. For some applications, driving includes driving the electrode device to apply the current not responsively to any physiological parameters sensed by any device directly or indirectly coupled to the control unit. For some applications, driving includes driving the electrode device to apply the current not responsively to any measure of a heart rate of the subject determined by the control unit.

There is additionally provided, in accordance with an embodiment of the present invention, apparatus including:
an electrode device, configured to be coupled to a site of the subject at risk of suffering from atrial fibrillation (AF), the site containing parasympathetic nervous tissue; and a control unit, configured to delay electrical remodeling of an atrium of the subject that may be caused by the AF, by:

driving the electrode device to apply an electrical current to the site, and configuring the current to stimulate the nervous tissue in the site.

There is yet additionally provided, in accordance with an embodiment of the present invention, a method including:

applying an electrical current, at a first strength on average, to a site of a subject containing parasympathetic nervous tissue;

configuring the current to stimulate the nervous tissue in the site;

performing at least one action selected from the group consisting of: sensing an occurrence of an episode of atrial fibrillation (AF), and predicting an imminent episode of the AF; and responsively to the performing, applying the current at a second strength on average during a strength reduction period having a duration of at least one minute, which second strength is less than the first strength.

In an embodiment, the site is selected from the group consisting of: a vagus nerve, an epicardial fat pad, a sinoatrial (SA) node fat pad, a pulmonary vein, a carotid artery, a carotid sinus, a coronary sinus, a vena cava vein, a jugular vein, an azygos vein, an innominate vein, and a subclavian vein, and applying the current includes applying the current to the selected site.

In an embodiment, performing includes sensing the occurrence of the episode of the AF, and applying the current at the second strength includes during the strength reduction period includes applying the current at the second strength during the episode.

In an embodiment, performing includes predicting the imminent episode of the AF.

For some applications, the method includes, upon a conclusion of the strength reduction period, configuring the current to reduce a heart rate of the subject, upon sensing that the episode of the AF has not terminated and that the subject has an elevated heart rate.

For some applications, applying the current at the second strength includes withholding applying the current.

For some applications, the strength reduction period has a duration of at least one minute, and applying the current at the second strength on average includes applying the current at the second strength on average during the strength reduction period having the duration of at least one minute.

For some applications, the method includes identifying that the subject is at risk of suffering from AF, and applying the current at the first strength includes, responsively to the identifying, reducing a risk of the occurrence of the episode of the AF by applying the current at the first strength.

For some applications, applying the current at the first strength includes applying the current at the first strength at least once during each of seven consecutive 48-hour periods.

For some applications, identifying that the subject is at risk includes identifying that the subject suffers from a condition selected from the group consisting of: paroxysmal AF, self-terminating AF episodes, an enlarged atrium, multiple atrial premature beats (APBs), mitral stenosis, heart failure, thyrotoxicosis, hypertension, and atrial flutter. Typically, identifying includes identifying by a medical professional that the subject is at risk.

In an embodiment, applying the current at the first strength includes applying the current at the first strength even in the absence of a prediction of an imminent episode of the AF. In an embodiment, applying the current at the first strength includes applying the current at the first strength in the absence of a prediction of an imminent episode of the AF. In an embodiment, applying the current at the first strength includes detecting normal sinus rhythm (NSR) of the subject, and applying the current at the first strength during the detected NSR.

In an embodiment, applying the current at the first strength does not include configuring the current to achieve a target heart rate or a target heart rate range of the subject.

for some applications, applying the current at the first strength includes commencing applying at least 24 hours after the identifying.

For some applications, applying the current at the first strength includes:

applying, during stimulation periods that alternate with rest periods, the current during "on" periods that alternate with low stimulation periods, the "on" periods having on average an "on" duration equal to at least 1 second, and the low stimulation periods having on average a low stimulation duration equal to at least 50% of the "on" duration;

setting the current applied on average during the low stimulation periods to be less than 20% of the current applied on average during the "on" periods;

setting the current applied on average during the rest periods to be less than 20% of the current applied on average during the "on" periods; and setting the rest periods to have on average a rest period duration equal to at least a cycle duration that equals a duration of a single "on" period plus a duration of a single low stimulation period, and the stimulation periods to have on average a stimulation period duration equal to at least five times the rest period duration.

For some applications, the site includes a sinoatrial (SA) node fat pad, and applying the current at the first strength includes applying the current to the SA node fat pad.

In an embodiment, the site includes the vagus nerve, and applying the current at the first strength includes applying the current to the vagus nerve. In an embodiment, applying the current at the first strength includes configuring the current to induce propagation of efferent action potentials traveling towards a heart of the subject, and suppress artificially-induced afferent action potentials traveling towards a brain of the subject.

In an embodiment, applying the current at the first strength includes configuring the current so as to minimize an effect of the applying of the current on a heart rate of the subject. For some applications, applying the current at the first strength includes:

setting a threshold heart rate;

sensing the heart rate of the subject;

comparing the sensed heart rate with the threshold heart rate; and applying the current at the first strength upon finding that the sensed heart rate is less than the threshold heart rate.

In an embodiment, applying the current at the first strength includes applying the current in a series of bursts, each of which bursts includes one or more pulses. For some applications, the series of bursts includes at least first and second bursts, the first burst including a plurality of the pulses, and the second burst including at least one of the pulses, and applying the current at the first strength includes setting (a) a pulse repetition interval (PRI) of the first burst to be on average at least 20 ms, (b) an interburst interval between initiation of the first burst and initiation of the second burst to be less than 10 seconds, (c) an interburst gap between a conclusion of the first burst and the initiation of the second burst to have a duration greater than the average PRI, and (d)

a burst duration of the first burst to be less than a percentage of the interburst interval, the percentage being less than 67%.

For some applications, applying the current at the first strength includes:

applying, during "on" periods that alternate with low stimulation periods, at least one of the "on" periods having an "on" duration of at least three seconds, and including at least three of the bursts, and at least one of the low stimulation periods immediately following the at least one of the "on" periods having a low stimulation duration equal to at least 50% of the "on" duration;

setting the current applied on average during the low stimulation periods to be less than 20% of the current applied on average during the "on" periods; and during at least one transitional period of the at least one of the "on" periods, ramping a number of pulses per burst, the at least one transitional period selected from the group consisting of: a commencement of the at least one of the "on" periods, and a conclusion of the at least one of the "on" periods.

In an embodiment, applying the current at the first strength includes synchronizing at least a portion of the bursts with a feature of a cardiac cycle of the subject. For example, the feature of the cardiac cycle may include a P-wave, and applying the current at the first strength includes synchronizing the at least a portion of the bursts with the P-wave. Alternatively, the feature of the cardiac cycle may include a R-wave, and applying the current at the first strength includes synchronizing the at least a portion of the bursts with the R-wave.

There is also provided, in accordance with an embodiment of the present invention, apparatus including:

an electrode device, configured to be coupled to a site of the subject at risk of suffering from atrial fibrillation (AF), the site containing parasympathetic nervous; and a control unit, configured to:

drive the electrode device to apply an electrical current to the site at a first strength on average, configure the current to stimulate the nervous tissue in the site, perform at least one action selected from the group consisting of: sensing an occurrence of an episode of atrial fibrillation (AF), and predicting an imminent episode of the AF, and responsively to the performance, apply the current at a second strength on average during a strength reduction period having a duration of at least one minute, which second strength is less than the first strength.

There is further provided, in accordance with an embodiment of the present invention, a method including:

identifying that a subject is at risk of suffering from atrial fibrillation (AF); and responsively to the identifying, reducing a risk of an occurrence of an episode of the AF by:

coupling an electrode device to a site of a subject containing parasympathetic nervous tissue, driving, by a control unit, the electrode device to apply an electrical current to the site not responsively to any physiological parameters sensed by any device directly or indirectly coupled to the control unit, and configuring the current to stimulate autonomic nervous tissue in the site.

In an embodiment, the site is selected from the group consisting of: a vagus nerve, an epicardial fat pad, a sinoatrial (SA) node fat pad, a pulmonary vein, a carotid artery, a carotid sinus, a coronary sinus, a vena cava vein, a jugular vein, an azygos vein, an innominate vein, and a subclavian vein, and applying the current includes applying the current to the selected site.

In an embodiment, driving includes driving the electrode device to apply the current at least once during each of seven consecutive 48-hour periods.

In an embodiment, the site includes the vagus nerve, and applying the current includes applying the current to the vagus nerve. In an embodiment, configuring includes configuring the current to induce propagation of efferent action potentials traveling towards a heart of the subject, and suppress artificially-induced afferent action potentials traveling towards a brain of the subject.

There is still further provided, in accordance with an embodiment of the present invention, apparatus including:

an electrode device, configured to be coupled to a site of the subject at risk of suffering from atrial fibrillation (AF), the site containing parasympathetic nervous tissue; and a control unit, configured to reduce a risk of an occurrence of an episode of the AF by:

driving the electrode device to apply an electrical current to the site not responsively to any physiological parameters sensed by any device directly or indirectly coupled to the control unit, and configuring the current to stimulate the nervous tissue in the site.

There is additionally provided, in accordance with an embodiment of the present invention, a method including:

setting a threshold heart rate;

sensing a heart rate of a subject;

comparing the sensed heart rate with the threshold heart rate;

upon finding that the sensed heart rate is less than the threshold heart rate, applying a current to a site of the subject containing parasympathetic nervous tissue; and configuring the current to increase vagal tone of the subject by stimulating the nervous tissue in the site, and to minimize an effect of the applying of the current on a heart rate of the subject.

In an embodiment, the site is selected from the group consisting of: a vagus nerve, an epicardial fat pad, a sinoatrial (SA) node fat pad, a pulmonary vein, a carotid artery, a carotid sinus, a coronary sinus, a vena cava vein, a jugular vein, an azygos vein, an innominate vein, a subclavian vein, a right ventricle, and a right atrium, and applying the current includes applying the current to the selected site.

In an embodiment, setting the threshold heart rate includes setting the threshold heart rate to a percentage of a normal heart rate for the subject. Alternatively, setting the threshold heart rate includes setting the threshold heart rate to a percentage of a normal heart rate for typical subjects.

There is yet additionally provided, in accordance with an embodiment of the present invention, apparatus including:

an electrode device, configured to be coupled to a site of a subject containing parasympathetic nervous tissue; and a control unit, configured to:

store a threshold heart rate, sense a heart rate of the subject, compare the sensed heart rate to the threshold heart rate, and upon finding that that the sensed heart rate is less than the threshold heart rate, drive the electrode device to apply a current to the site, and to configure the current to (a) increase vagal tone of the subject by stimulating the nervous tissue in the site, and (b) minimize an effect of the applying of the current on a heart rate of the subject.

There is also provided, in accordance with an embodiment of the present invention, a method including:

identifying that a subject is at risk of suffering from atrial fibrillation (AF); and responsively to the identifying, reducing a risk of an occurrence of an episode of the AF by:

detecting normal sinus rhythm (NSR) of the subject, during the detected NSR, applying an electrical current to a site of the subject containing parasympathetic nervous tissue, and configuring the current to stimulate the nervous tissue in the site.

In an embodiment, the site is selected from the group consisting of: a vagus nerve, an epicardial fat pad, a sinoatrial (SA) node fat pad, a pulmonary vein, a carotid artery, a carotid sinus, a coronary sinus, a vena cava vein, a jugular vein, an azygos vein, an innominate vein, and a subclavian vein, and applying the current includes applying the current to the selected site.

In an embodiment, applying the current includes configuring the current so as to minimize an effect of the applying of the current on a heart rate of the subject.

For some applications, applying the current includes:

setting a threshold heart rate;

sensing the heart rate of the subject;

comparing the sensed heart rate with the threshold heart rate; and applying the current upon finding that the sensed heart rate is less than the threshold heart rate.

For some applications, applying the current includes:

applying the current at a first strength on average;

sensing the occurrence of the episode of the AF; and responsively to the sensing, applying the current at a second strength on average during a strength reduction period having a duration of at least one minute, which second strength is less than the first strength.

For some applications, applying the current at the second strength includes withholding applying the current. For some applications, applying the current includes, upon a conclusion of the strength reduction period, configuring the current to reduce a heart rate of the subject, upon sensing that the episode of the AF has not terminated and that the subject has an elevated heart rate.

For some applications, applying the current includes:

applying the current at a first strength on average;

predicting that the occurrence of the episode of the AF is imminent; and responsively to the predicting, applying the current at a second strength on average during a strength reduction period having a duration of at least one minute, which second strength is less than the first strength.

For some applications, applying the current at the second strength includes withholding applying the current.

There is further provided, in accordance with an embodiment of the present invention, apparatus including:

an electrode device, configured to be coupled to a site of a subject at risk of suffering from atrial fibrillation (AF), the site containing parasympathetic nervous tissue; and a control unit, configured to reduce a risk of an occurrence of an episode of the AF by:

detecting normal sinus rhythm (NSR) of the subject, during the detected NSR, driving the electrode device to apply an electrical current to the site, and configuring the current to stimulate the nervous tissue in the site.

There is further provided, in accordance with an embodiment of the present invention, a method for treating a subject suffering from atrial fibrillation, including:

applying a current to a site of the subject selected from the group consisting of: a vagus nerve of the subject, an epicardial fat pad of the subject, a pulmonary vein of the subject, a carotid artery of the subject, a carotid sinus of the subject, a vena cava vein of the subject, a jugular vein of the subject, an azygos vein of the subject, an innominate vein of the subject, and a subclavian vein of the subject; and configuring the current to increase vagal tone of the subject, and to minimize an effect of the applying of the current on a heart rate of the subject, so as to treat the condition.

In an embodiment, the method includes applying a pacing signal to a heart of the subject in conjunction with applying the current to the site.

In an embodiment, the method includes sensing a heart rate of the subject, and configuring the current includes configuring the current using a feedback loop, an input of which is the sensed heart rate.

There is further provided, in accordance with an embodiment of the present invention, a method for treating a subject suffering from a condition, including:

applying a current to a site of the subject selected from the group consisting of: a vagus nerve of the subject, and epicardial fat pad of the subject, a pulmonary vein of the subject, a carotid artery of the subject, a carotid sinus of the subject, a vena cava vein of the subject, a jugular vein of the subject, an azygos vein of the subject, an innominate vein of the subject, and a subclavian vein of the subject; and configuring the current so as to delay electrical remodeling of an atrium of the subject caused by the condition.

In an embodiment, configuring the current includes configuring the current so as to prevent electrical remodeling of the atrium caused by the condition.

In an embodiment, the condition includes heart failure (HF), and configuring the current includes configuring the current so as to prevent the electrical remodeling caused by the HF.

In an embodiment, the condition includes both atrial fibrillation (AF) and heart failure (HF), and configuring the current includes configuring the current so as to prevent the electrical remodeling caused by the AF and the HF.

In an embodiment, the method includes administering a drug for treating the condition.

In an embodiment, no drug is administered for treating the condition during a period beginning about 24 hours before initiation of application of the current and ending upon the initiation of the application of the current.

In an embodiment, the condition includes atrial fibrillation (AF), and configuring the current includes configuring the current so as to prevent the electrical remodeling caused by the AF. For some applications, applying the current includes detecting an occurrence of the AF, and applying the current responsively to the detecting. For some applications, applying the current includes applying the current not responsively to detecting an occurrence of the AF.

There is yet additionally provided, in accordance with an embodiment of the present invention, a method including:

applying a current to a site of a subject selected from the group consisting of: a vagus nerve of the subject, an epicardial fat pad of the subject, a pulmonary vein of the subject, a carotid artery of the subject, a carotid sinus of the subject, a vena cava vein of the subject, a jugular vein of the subject, an azygos vein of the subject, an innominate vein of the subject, and a subclavian vein of the subject; and configuring the current to reduce mechanical tension on at least one atrium of the subject, so as to reduce a risk of an occurrence of atrial fibrillation (AF).

In an embodiment, the method includes administering to the subject a drug for treating the AF.

There is still further provided, in accordance with an embodiment of the present invention, a method for treating a subject, including:

applying a current to a site of the subject selected from the group consisting of: a vagus nerve of the subject, and epicardial fat pad of the subject, a pulmonary vein of the subject, a carotid artery of the subject, a carotid sinus of the subject, a vena cava vein of the subject, a jugular vein of the subject, an azygos vein of the subject, an innominate vein of the subject, and a subclavian vein of the subject; and configuring the current so as to have an antiarrhythmic effect on an atrium of the subject.

For some applications, the site includes a right vagus nerve of the subject, and applying the current includes applying the current to the right vagus nerve.

In an embodiment, the method includes administering an antiarrhythmic drug to the subject in conjunction with applying the current.

For some applications, configuring the current includes configuring the current so as to induce rhythmic vagal activity in the subject.

In an embodiment, applying the current includes applying the current to the site intermittently during alternating "on" and "off" periods. For some applications, applying the current intermittently includes setting each of the "on" periods to have a duration of between about 1 and about 15 seconds, and each of the "off" periods to have a duration of between about 5 and about 20 seconds.

In an embodiment, the site includes the vagus nerve, and applying the current includes applying the current to the vagus nerve. For some applications, applying the current includes applying a stimulating current, which is capable of inducing action potentials in a first set and a second set of nerve fibers of the vagus nerve, and an inhibiting current, which is capable of inhibiting the induced action potentials traveling in the second set of nerve fibers, the nerve fibers in the second set having generally larger diameters than the nerve fibers in the first set. For some applications, applying the current includes applying a stimulating current, which is capable of inducing action potentials in the vagus nerve, and an inhibiting current, which is capable of inhibiting action potentials induced by the stimulating current and traveling in the vagus nerve in an afferent direction toward a brain of the subject.

In an embodiment, applying the current includes applying the current in respective bursts of pulses in each of a plurality of cardiac cycles of the subject. For some applications, applying the current includes applying a first pulse of each of the bursts after a delay from a sensed feature of an electrocardiogram (ECG) of the subject.

In an embodiment, the method includes sensing a physiological parameter of the subject, and configuring the current includes configuring the current at least in part responsively to the sensed physiological parameter. For some applications, sensing the physiological parameter includes sensing a heart rate of the subject.

In an embodiment, configuring the current includes configuring the current so as to minimize an effect of the applying of the current on a heart rate of the subject.

In an embodiment, applying the current includes applying the current in respective bursts of pulses in each of a plurality of cardiac cycles of the subject. For some applications, applying the current includes applying the current to a left vagus nerve of the subject. For some applications, applying the current includes configuring each of the pulses to have a duration of between about 200 microseconds and about 2.5 milliseconds. For some applications, applying the current includes configuring each of the pulses to have a duration of between about 2.5 and about 5 milliseconds. For some applications, applying the current includes configuring each of the bursts to have a duration of between about 0.2 and about 40 milliseconds. For some applications, applying the current includes configuring each of the bursts to contain between about 1 and about 10 pulses. For some applications, applying the current includes configuring the pulses within each of the bursts to have a pulse repetition interval of between about 2 and about 10 milliseconds. For some applications, applying the current includes configuring the pulses to have an amplitude of between about 0.5 and about 5 mA. For some applications, applying the current includes applying the bursts less than every heartbeat of the subject. For some applications, applying the current includes applying the bursts once per heartbeat of the subject. For some applications, applying the current includes applying the current to the site intermittently during alternating "on" and "off" periods, each of the "on" periods having a duration of at least about 1 second. For some applications, applying the current includes applying each of the bursts after a variable or fixed delay following a P-wave of the subject. For some applications, the delay has a duration equal to less than about 50 ms, while for other applications the delay has a duration equal to between about two-thirds and about 90% of a duration of a cardiac cycle of the subject. For some applications, applying the current includes substantially continuously measuring the duration of the cardiac cycle.

In an embodiment, applying the current includes applying the current in respective bursts of pulses in each of a plurality of cardiac cycles of the subject. For some applications, applying the current includes configuring each of the pulses to have a duration of between about 100 microseconds and about 2.5 milliseconds. For some applications, applying the current includes configuring each of the bursts to have a duration of between about 1 and about 180 milliseconds. For some applications, applying the current includes configuring each of the bursts to contain between about 1 and about 10 pulses. For some applications, applying the current includes configuring the pulses within each of the bursts to have a pulse repetition interval of between about 1 and about 20 milliseconds. For some applications, applying the current includes configuring the pulses to have an amplitude of between about 0.1 and about 9 mA. For some applications, applying the current includes applying the bursts once every second heartbeat. For some applications, applying the current includes applying the bursts once every third heartbeat. For some applications, applying the current includes applying the current to the site intermittently during alternating "on" and "off" periods, each of the "on" periods having a duration of at least about 1 second. For some applications, applying the current includes applying each of the bursts after a delay following an R-wave of the subject, the delay having a duration of about 100 milliseconds.

In an embodiment, applying the current includes applying the current in respective bursts of between about 1 and about 10 pulses in each of a plurality of cardiac cycles of the subject, and applying a first pulse of each of the bursts after a delay of about 100 milliseconds after a sensed R-wave of an electrocardiogram (ECG) of the subject. For some applications, applying the current includes configuring each of the bursts to contain about three pulses. For some applications, applying the current includes varying a number of the pulses in each of the bursts responsive to a sensed parameter of a respiratory cycle of the subject. For some applications, applying the current includes varying a number of the pulses in each of the bursts responsive to a sensed heart rate of the subject. For some applications, the site includes the vagus nerve, and applying the current includes applying the current to the vagus nerve, and, responsive to a sensed heart rate of the subject, varying a number of nerve fibers of the vagus nerve that are recruited.

For some applications, the site includes the vagus nerve, and applying the current includes applying the current to the vagus nerve, and, responsive to a sensed parameter of a respiratory cycle of the subject, varying a number of nerve fibers of the vagus nerve that are recruited. For some applications, applying the current includes cycling between a first set of parameters and a second set of parameters. For some applications, cycling includes applying each set of parameters for less than about 15 seconds. For some applications, cycling includes applying each set of parameters for between about 1 and about 4 seconds. For some applications, the first set of parameters includes a first amplitude, the second set of parameters includes a second amplitude, greater than the first amplitude, and applying the current includes varying a number of nerve fibers of the vagus nerve that are recruited by cycling between the first set of parameters and the second set of parameters.

For some applications, cycling includes synchronizing application of the first set of parameters with inhalation by the subject, and synchronizing application of the second set of parameters with exhalation by the subject. For some applications, at least one of the first and second sets of parameters includes a pulse repetition interval of between about 4 and about 20 milliseconds, and applying the current includes cycling between the first and second sets of parameters. For some applications, at least one of the first and second sets of parameters includes a pulse width of between about 0.1 and about 2 milliseconds, and applying the current includes cycling between the first and second sets of parameters. For some applications, the first set of parameters includes application of the current at one pulse per each of the bursts, the second set of parameters includes application of the current at about three pulses per each of the bursts, and applying the current includes cycling between the first and second sets of parameters.

There is still further provided, in accordance with an embodiment of the present invention, apparatus for treating a subject suffering from a condition, including:

an electrode device, adapted to be coupled to a site of the subject selected from the group consisting of: a vagus nerve of the subject, an epicardial fat pad of the subject, a pulmonary vein of the subject, a carotid artery of the subject, a carotid sinus of the subject, a vena cava vein of the subject, a jugular vein of the subject, an azygos vein of the subject, an innominate vein of the subject, and a subclavian vein of the subject; and a control unit, adapted to:

drive the electrode device to apply an electrical current to the site, and configure the current so as to delay electrical remodeling of an atrium of the subject caused by the condition.

There is also provided, in accordance with an embodiment of the present invention, apparatus including:

an electrode device, adapted to be coupled to a site of a subject selected from the group consisting of: a vagus nerve of the subject, an epicardial fat pad of the subject, a pulmonary vein of the subject, a carotid artery of the subject, a carotid sinus of the subject, a vena cava vein of the subject, a jugular vein of the subject, an azygos vein of the subject, an innominate vein of the subject, and a subclavian vein of the subject; and a control unit, adapted to:

drive the electrode device to apply an electrical current to the site, and configure the current to reduce mechanical tension on at least one atrium of the subject, so as to reduce a risk of an occurrence of atrial fibrillation (AF).

There is still further provided, in accordance with an embodiment of the present invention, apparatus for treating a subject, including:

an electrode device, adapted to be coupled to a site of the subject selected from the group consisting of: a vagus nerve of the subject, an epicardial fat pad of the subject, a pulmonary vein of the subject, a carotid artery of the subject, a carotid sinus of the subject, a vena cava vein of the subject, a jugular vein of the subject, an azygos vein of the subject, an innominate vein of the subject, and a subclavian vein of the subject; and a control unit, adapted to:

drive the electrode device to apply an electrical current to the site, and configure the current so as to have an antiarrhythmic effect on an atrium of the subject.

The present invention will be more fully understood from the following detailed description of embodiments thereof, taken together with the drawings, in which:

BRIEF DESCRIPTION OF THE DRAWINGS

FIG. 3 is a simplified perspective illustration of a multipolar point electrode device applied to a vagus nerve, in accordance with an embodiment of the present invention;

FIG. 7 is a schematic illustration of a stimulation regimen, in accordance with an embodiment of the present invention; and FIG. 8 is a schematic illustration of a stimulation regimen, in accordance with an embodiment of the present invention.

DETAILED DESCRIPTION OF EMBODIMENTS

Figure 1:
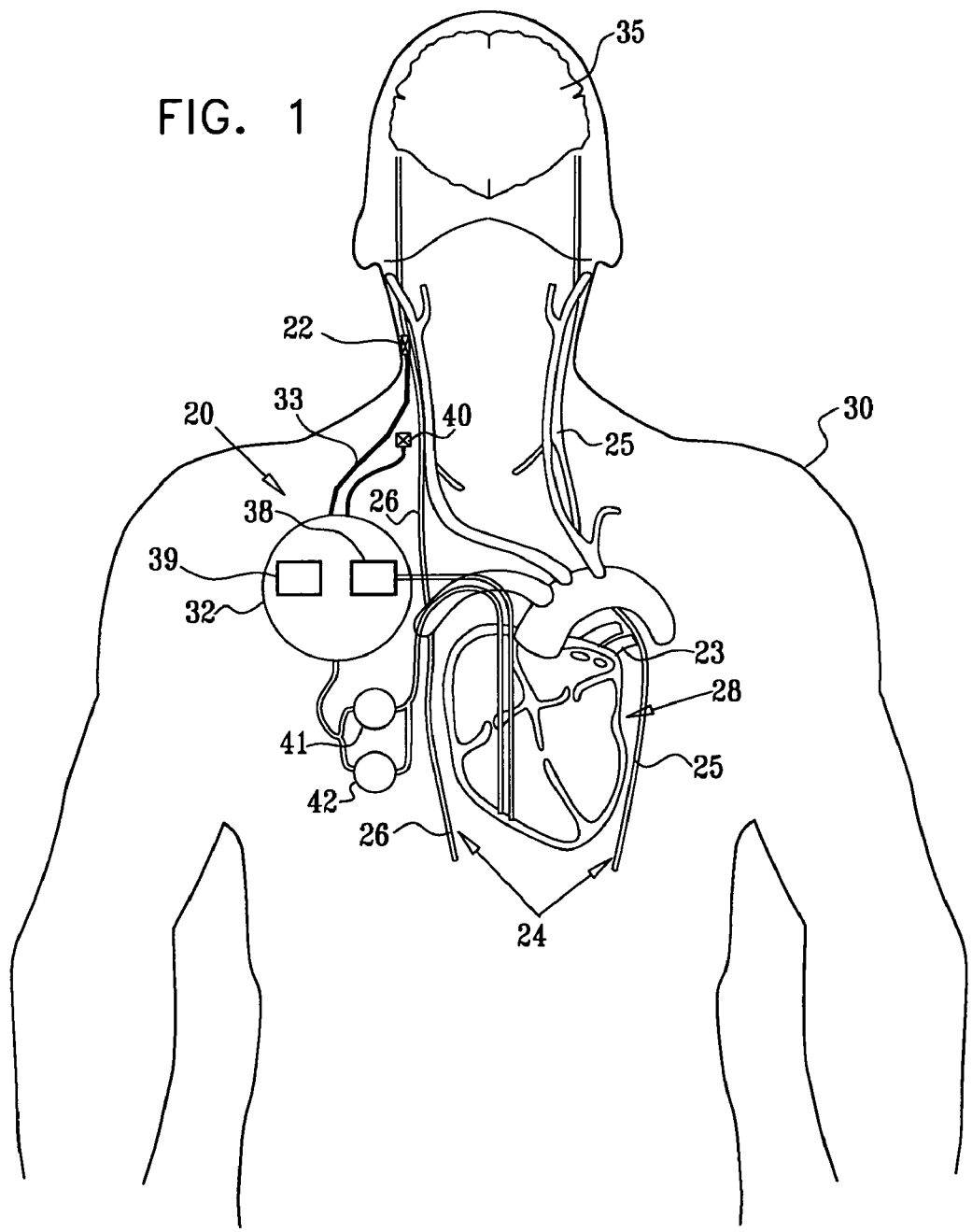
FIG. 1 is a schematic illustration of apparatus for treating a subject, in accordance with an embodiment of the present invention.

FIG. 1 is a schematic illustration of apparatus 20 for treating a subject 30, in accordance with an embodiment of the present invention. Apparatus 20 comprises at least one electrode device 22, which is applied to a site of the subject selected from the group consisting of: a vagus nerve 24 (either a left vagus nerve 25 or a right vagus nerve 26), which innervates a heart 28 of subject 30, an epicardial fat pad (e.g., a sinoatrial (SA) node fat pad, or an atrioventricular (AV) node fat pad), a pulmonary vein, a carotid artery, a carotid sinus, a coronary sinus, a vena cava vein, a jugular vein, an azygos vein, an innominate vein, and a subclavian vein. Alternatively or additionally, the site is selected from the group consisting of: a right ventricle, a right atrium, and other parasympathetic tissue that innervates heart 28. "Vagus nerve," and derivatives thereof, as used in the present application including the claims, is to be understood to include portions of the left vagus nerve, the right vagus nerve, and branches of the vagus nerve such as the cervical or thoracic vagus nerve, superior cardiac branch, and inferior cardiac branch.

Apparatus 20 further comprises an implanted or external control unit 32, which typically communicates with electrode device 22 over a set of leads 33. For some applications, apparatus 20 comprises two electrode devices 22, one of which is applied to left vagus nerve 25, and the other to right vagus nerve 26.

Control unit 32 is adapted to drive electrode device 22 to apply signals to the site, and to configure the current to stimulate autonomic nervous tissue in the site. The control unit typically configures the applied signals to induce the propagation of efferent nerve impulses towards heart 28. The control unit configures the signals based on the particular application, by setting one or more parameters of the signals, such as:

frequency of pulses within a pulse burst, e.g., for n pulses during a burst lasting t milliseconds, the burst has a frequency of 1000 n/t Hz;
amplitude;
pulse width;
number of pulse delivered per heartbeat (pulses per trigger, or PPT);
duty cycle;
pulse polarity; and
timing within the cardiac cycle.

In an embodiment of the present invention, a method for treating subject 30 who is at risk of suffering from atrial fibrillation (AF) comprises reducing a risk of an occurrence of an episode of the AF by applying an electrical current to a site of subject 30 selected from the group consisting of: vagus nerve 24 (either left vagus nerve 25 or right vagus nerve 26), an epicardial fat pad, a pulmonary vein, a carotid artery, a carotid sinus, a coronary sinus, a vena cava vein, a jugular vein, an azygos vein, an innominate vein, and a subclavian vein. Alternatively or additionally, the site is selected from the group consisting of: a right ventricle, a right atrium, and other parasympathetic tissue that innervates heart 28. For some applications, control unit 32 of apparatus 20 drives electrode device 22 to apply the electrical current.

For some applications, the current is applied intermittently during alternating "on" and "off" periods. Typically, each of the "on" periods has an "on" duration equal to at least 1 second (e.g., between 1 and 10 seconds, such as about 3 seconds), and each of the "off" periods has an "off" duration equal to at least 50% of the "on" duration, e.g., at least 100% or 200% of the "on" duration, such as about 9 seconds.

For some applications, control unit 32 is configured to apply the current on a chronic, long-term basis, even when the subject is not currently experiencing an episode of the AF, and even in the absence of a prediction of an imminent episode of the AF. The current is thus typically applied during normal sinus rhythm (NSR). For some applications, chronically applying the current comprises applying the current at least once during each of seven consecutive 48-hour periods, such as at least once during each of 14 consecutive 24-hour periods, or at least once during each of 28 consecutive 12-hour periods. For some applications, applying the current comprises applying at least 100 pulses of the current per day.

For some applications, chronically applying the current comprises applying the current at least once per day during a three-week period. For example, apparatus 20 may be implanted and configured to apply the current for a period of at least three months, a year, or three years, which period includes at least one three-week period during which the current is applied at least once per day, e.g., at least twice per day, and/or for at least 30 minutes per day, such as at least 60 minutes per day. Alternatively, the current is applied chronically, but less frequently, such as at least once every 48 hours, at least twice per week, or at least once per week. For some applications, applying the current at least once per day comprises applying at least a total 100 pulses per day.

In an embodiment, apparatus 20 comprises a sensor adapted to detect normal sinus rhythm (NSR) and generate a sensor signal responsive thereto, and control unit 32 is adapted to receive the sensor signal, and to drive electrode device 22 to apply the current responsive to the sensor signal.

In an embodiment of the present invention, subject 30 is determined to be at risk of suffering from AF by identifying that the subject suffers from at least one of the following conditions:
paroxysmal AF;
self-terminating AF episodes;
an enlarged atrium;
multiple atrial premature beats (APBs);
mitral stenosis;
heart failure;
thyrotoxicosis;
hypertension; and
atrial flutter.

Alternatively or additionally, the subject is determined to be at risk of suffering from AF by identifying that the subject has undergone an interventional heart procedure, such as coronary bypass surgery or valve replacement surgery.

For some applications, this determination is made after the subject has suffered from at least one episode of the AF, while for other applications, the determination is made prior to the subject suffering from any known episodes of the AF. Typically, the identification that the subject is at risk is made by a medical professional. Typically, reducing the risk comprises reducing the risk in the absence of a determination by any device directly or indirectly coupled to the electrode device that the subject is at risk of suffering from the AF. In other words, the medical decision to implant apparatus 20 is typically made by a medical professional who identifies that the subject is at risk of suffering from AF, but apparatus 20 itself does not assess the subject's risk of suffering from AF, or any episodes or particular episode thereof.

For some applications, control unit 32 applies the current not responsively to any physiological parameters sensed by any device coupled to electrode device 22 or to control unit 32 (e.g., the control unit itself or a sensor coupled to the control unit).

For some applications, the control unit applies the current not responsively to any measure of a heart rate of the subject (which may be expressed as a heart rate or interval, e.g., an R-R interval) determined by the control unit. For these application, control unit 32 does not configure any parameters of the applied current responsively to any measure of the heart rate, including any timing parameters of the current application. For these applications, although the control unit does not apply the current responsively to the measure of the heart rate, the control unit may apply the current responsively to other physiological measures, such as described herein. For example, the control unit may synchronize the applied current to one or more features of a cardiac cycle of the subject, such as described herein.

Control unit 32 typically does not configure the current to achieve regulation of a heart rate of the subject, such as to achieve a target heart rate or range. For some applications, the current is configured to minimize an effect of the applying of the current on a heart rate of the subject, as described hereinbelow.

Alternatively, control unit 32 is configured to receive and analyze one or more sensed physiological parameters or other parameters of subject 30, such as ventricular and/or atrial rate, electrocardiogram (ECG), blood pressure, indicators of decreased cardiac contractility, cardiac output, norepinephrine concentration, baroreflex sensitivity, or motion of the subject. In order to receive these sensed parameters, control unit 32 may comprise, for example, an ECG monitor 38, connected to a site on the subject's body such as heart 28, for example using one or more subcutaneous sensors or ventricular and/or atrial intracardiac sensors. The control unit may also comprise an accelerometer 39 for detecting motion of the subject. Alternatively, ECG monitor 38 and/or accelerometer 39 comprise separate implanted devices placed external to control unit 32, and, optionally, external to the subject's body. Alternatively or additionally, control unit 32 receives signals from one or more physiological sensors 40, such as blood pressure sensors. For some applications, control unit 32 comprises or is coupled to an implantable cardioverter defibrillator (ICD) 41 and/or a pacemaker 42 (e.g., a bi-ventricular or standard pacemaker).

In some embodiments of the present invention, upon sensing an occurrence of an episode of the AF, the control unit reduces a strength of the current, e.g., withholds applying the current. The inventors believe that application of the current sometimes prolongs episodes of the AF, so reducing the strength of or withholding the current generally allows episodes to resolve more quickly than they would during application of the current at full strength. Similarly, for some applications, upon predicting an imminent episode of the AF, the control unit reduces the strength of the current, e.g., withholds applying the current. For some applications, techniques for sensing or predicting the imminent episode of the AF are used that are described in above-mentioned U.S. Pat. No. 5,522,854 to Ideker et al., U.S. Pat. No. 5,658,318 to Stroetmann et al., U.S. Pat. No. 7,050,846 to Sweeney et al., U.S. Pat. No. 5,578,061 to Stroetmann et al., and/or other references mentioned in the Background of the Invention section hereinabove.

For some applications, control unit 32 senses the occurrence of the episode of AF by analyzing an ECG signal generated by ECG monitor 38. In order to detect rapid atrial activity indicative of AF, the analysis may include one or more of the following:

P-wave analysis;
analysis of ventricular response rate and/or ventricular response variability;
sensed pressure, such as atrial pressure, sensed venous pressure, and/or sensed arterial pressure;
the relationship(s) between one or more of the sensed pressures and sensed ventricular contractions (in the case of arterial pressure, such relationship is an indication of pulse deficit); and/or
analysis of the duration of the isoelectrical segment of the ECG, optionally using the technique described in the above-cited article by Wijffels et al., entitled, "Atrial fibrillation begets atrial fibrillation." A duration greater than a first threshold value is typically indicative of NSR, while a duration less than a second threshold value, the second threshold value less than or equal to the first threshold value, is typically indicative of AF.

Control unit 32 itself may perform this analysis, or it may transmit data for analysis by an external processor (not shown).

Typically, apparatus 20 is programmable by a physician, such as by using an external console wirelessly in communication with control unit 32. For some applications, the apparatus provides notification of various occurrences, such as the initiation of AF, the initiation of treatment, or a mechanical failure. The apparatus may provide such notifications by various means, including generating a tone, vibrating, and/or wirelessly communicating with a local or remote receiver, such as one located at a medical facility.

In an embodiment of the present invention, apparatus 20 comprises a sensing unit configured to detect whether applying the current causes one or more cardiac contractions, and control unit 32 is configured, responsively to finding that applying the current causes the contractions, to reduce a strength of the current to a level insufficient to cause the contractions. Typically, the sensing unit comprises ECG monitor 38.

In an embodiment of the present invention, upon sensing an occurrence of an episode of the AF, control unit 32 reduces a strength of the current, e.g., withholds applying the current, typically during a strength reduction period having a duration of at least one minute, e.g., at least 5 minutes, at least 10 minutes, at least 20 minutes, or at least one hour. The inventors believe that application of the current sometimes prolongs episodes of AF, so reducing the strength of or withholding the current generally allows episodes to resolve more quickly than they would during application of the current at full strength. Similarly, for some applications, upon predicting an imminent episode of the AF, control unit 32 reduces the strength of the current, e.g., withholds applying the current. For some applications, upon conclusion of the strength reduction period, the control unit configures the current to reduce a heart rate of the subject if the episode of AF has not terminated, and the subject has an elevated heart rate.

In an embodiment, control unit 32 is configured to apply the current during an episode of the AF, and is not configured to configure the current to resolve the episode. For some applications, the control unit is configured to apply the current during the episode and during at least one period not during the episode. For some applications, the control unit is configured to detect the episode, and to apply the current responsively to the detecting. For some applications, the control unit is configured to apply the current even during an episode of the AF, without configuring the current to resolve the episode.

In some embodiments of the present invention, control unit 32 applies the current in a series of bursts, each of which bursts includes at least one pulse. For some applications, the control unit synchronizes at least a portion of the bursts with a feature of a cardiac cycle of the subject, such as a P-wave or R-wave. Synchronization with the P-wave has the effect of automatically withholding stimulation during AF, because no P-wave is present during AF.

For some applications, control unit 32 applies the signals to the selected parasympathetic site in a series of bursts, each of which bursts includes at least one pulse. For some of these applications, during periods in which stimulation is being applied, one burst is applied during each cardiac cycle, or during every nth cardiac cycle, such as one burst every second or every third cardiac cycle, with one or more of the following parameters (collectively, these parameters are referred to hereinbelow as "typical stimulation parameters"):

- Timing of the stimulation: for example, each pulse may be initiated at about 100 milliseconds after an R-wave.
- Pulse duration: each pulse typically has a duration of between about 100 microseconds and about 2.5 milliseconds, e.g., about 1 millisecond.
- Pulse amplitude: the pulses are typically applied with an amplitude of between about 0.1 and about 9 mA, e.g., about 2.5 mA.
- Pulse repetition interval (PRI): the pulses within the burst of pulses typically have a PRI (the time from the initiation of a pulse to the initiation of the following pulse) of, on average, at least 20 ms, such as at least 30 ms, e.g., at least 50 ms or at least 75 ms; alternatively, the PRI may be between about 1 and about 20 milliseconds, e.g., about 6 milliseconds.
- Pulses per trigger (PPT): the burst of pulses typically contains between about 1 and about 10 pulses, e.g., 3 pulses or 4 pulses.
- Pulse period, i.e., burst duration (equal to the product of PRI and PPT): the burst of pulses typically has a total duration of between about 1 and about 180 milliseconds.
- Duty cycle: stimulation is typically applied once per heartbeat, once every second heartbeat, or once every third heartbeat.
- On/off status: for some applications, stimulation is always "on", i.e., constantly applied (in which case, parameters closer to the lower ends of the ranges above are typically used). For other applications, on/off cycles vary between a few seconds to several minutes, e.g., "on" for 15 seconds, "off" for 60 seconds.

Alternatively, the stimulation is not synchronized with the cardiac cycle. For some non-synchronized applications, the applicable parameters listed above are used, such as a PPT of 3 or 4 pulses. For some applications, the bursts are applied at a frequency (i.e., bursts per second) of 1 Hz or less, e.g., 0.5 Hz or less.

In an embodiment of the present invention, a method for enhancing or sustaining the efficacy of drug treatment for atrial fibrillation (AF) comprises administering a drug to subject 30 and applying signals to a site that innervates heart 28 of the subject, such as described in the above-mentioned U.S. application Ser. No. 10/866,601.

Atrial electrical remodeling, i.e., electrophysiological changes to the atria, commonly occurs in subjects suffering from AF. Such electrical remodeling is believed to be caused by the underlying heart condition that instigated the AF, and/or by the effect of the AF itself on the atria (see the above-cited article entitled, "Atrial fibrillation begets atrial fibrillation," by Wijffels et al.). As electrical remodeling becomes more severe, relapses into AF become more frequent and difficult to prevent. As a result, drug therapy for preventing such relapses becomes less effective. Vagal or other parasympathetic stimulation, using techniques described herein, typically delays or prevents (i.e., delays indefinitely) electrical remodeling. For subjects also receiving antiarrhythmic drug therapy, such delaying generally prolongs the effectiveness of the drug therapy. For some applications, control unit 32 configures the signals applied to the site using parameters described hereinbelow for applying vagal or other parasympathetic stimulation with minimum heart rate reduction.

For some applications, control unit 32 configures the current to reduce mechanical stress of heart 28, and/or to induce rhythmic vagal activity. Such rhythmic, synchronized vagal activity generally mimics normal vagal traffic, which is sometimes reduced in these subjects (who may, for example, suffer from heart failure or hypertension). Stable NSR typically results from such treatment, thereby generally reducing the occurrence of AF.

For example, stimulation may be applied by cycling between a first set and a second set of parameters, applying each set for less than about 15 seconds, e.g., for between about 1 and about 4 seconds. The first set of parameters may include: (a) a low amplitude, e.g., 2 mA, so as to recruit a relatively small number of nerve fibers, (b) optional synchronization with inhalation, and (c) one pulse per trigger (PPT), for example applied at about 300 milliseconds after an R-wave. The second set of parameters may include: (a) a greater amplitude, e.g., 3 mA, so as to recruit a greater number of fibers, (b) optional synchronization with exhalation, and (c) three PPT, applied at about 300 milliseconds after an R-wave. Both sets of parameters optionally include a pulse width of about 1 millisecond and/or a PRI that is on average at least 20 ms, such as at least 30 ms, e.g., at least 50 ms or at least 75 ms; alternatively, the PRI may be between about 4 and about 20 ms.

In an embodiment of the present invention, stimulation configured for inhibiting, delaying or preventing (i.e., delaying indefinitely) electrical remodeling in AF patients is applied in the absence of specific antiarrhythmic drug therapy. Such prevention of electrical remodeling alone is believed by the inventors to be therapeutically beneficial. For example, Takei et al., in their above-cited article, hypothesize, based on their experiments in anesthetized dogs, that vagal stimulation prior to atrial rapid pacing may protect the atrium from electrical remodeling.

In an embodiment of the present invention, a method for enhancing or sustaining the efficacy of a drug treatment for AF comprises administering a drug to the subject, applying signals to a parasympathetic site, and configuring the signals to reduce the mechanical tension on the atria. Such reduced mechanical tension generally reduces the risk of AF. For some applications, such stimulation is applied without administering the drug.

For some applications, such stimulation for the prevention of atrial remodeling (whether or not in conjunction with drug therapy) is applied generally constantly, using parameters described hereinbelow for applying stimulation with minimum heart rate reduction, or using the typical stimulation parameters described hereinabove. For other applications, such stimulation is only applied upon the detection of the occurrence of AF, such as by using one or more of the AF detection techniques described hereinabove.

In an embodiment of the present invention, control unit 32 configures the applied signals to have an antiarrhythmic effect on the atrium. Typical signal parameters in such a configuration include those described hereinbelow for applying stimulation with minimum heart rate reduction, or the typical stimulation parameters described hereinabove. The stimulation is typically applied to right vagus nerve 26, but may also be applied to left vagus nerve 25 or both vagus nerves together, or another of the parasympathetic sites listed hereinabove. For some applications, such antiarrhythmic stimulation is applied in conjunction with the rhythmic stimulation technique described hereinabove. For applications in which such antiarrhythmic stimulation is applied in combination with antiarrhythmic drug therapy, the combined treatment generally results in a synergistic effect.

In an embodiment of the present invention, the safety of a drug administered to subject 30 is improved by applying signals to vagus nerve 24 or another of the parasympathetic sites listed hereinabove, and configuring the signals so as to prevent adverse effects sometimes caused by the drug, such as repolarization abnormalities (e.g., prolongation of the QT interval), bradycardia, and/or ventricular tachyarrhythmia (e.g., ventricular fibrillation), such as using techniques described in the above-mentioned U.S. application Ser. No. 10/866,601.

In an embodiment of the present invention, stimulation is applied and configured to prevent atrial electrical remodeling caused by heart failure (see the above-cited article by Li D et al.). For some applications, such stimulation is applied to increase the efficacy and/or safety of a heart failure drug; for other applications, such stimulation is applied in the absence of specific drug therapy. Such prevention of electrical remodeling alone is believed by the inventors to be therapeutically beneficial. In an embodiment, stimulation is applied and configured to treat a subject suffering from both AF and heart failure, such as by preventing atrial electrical remodeling, and/or by increasing the efficacy and/or safety of one or more drugs for AF and/or heart failure.

In an embodiment of the present invention, a method for increasing vagal tone comprises applying signals to vagus nerve 24 or another of the parasympathetic sites listed hereinabove, and configuring the signals to deliver parasympathetic nerve stimulation to heart 28, while at the same time minimizing the heart-rate-lowering effects of the stimulation. Such treatment generally results in the beneficial effects of vagal or other parasympathetic stimulation that are not necessarily dependent on the heart-rate reduction effects of such stimulation. (See, for example, the above-cited article by Vanoli E et al.) Therefore, such stimulation is generally useful for treating conditions such as AF, heart failure, atherosclerosis, restenosis, myocarditis, cardiomyopathy, post-myocardial infarct remodeling, and hypertension. In addition, such treatment is believed by the inventors to reduce the risk of sudden cardiac death in some subjects (such as those with hypertrophic cardiomyopathy or congenital long QT syndrome).

Such parasympathetic stimulation is also beneficial for treating some conditions or under some circumstances in which heart rate reduction is not indicated or is contraindicated. For example, such parasympathetic stimulation is typically appropriate:

for treating heart failure subjects that suffer from bradycardia when taking beta-blockers;

at nighttime, when heart rate is naturally lower;

during exercise, such as when the heart rate is already within a desired range and further decreases may reduce exercise tolerance;

for subjects receiving heart-rate lowering drugs, who have achieved a heart rate within a desired range prior to beginning stimulation, and therefore would not benefit from further heart rate reduction;

for subjects suffering from low cardiac output, for whom heart rate reduction may further reduce cardiac output;

during acute myocardial infarction with cardiogenic shock;

for subjects who experience discomfort or a reduction in exercise capacity when the heart rate is reduced; and for subjects having a tendency towards bradycardia when receiving vagal or parasympathetic stimulation.

In an embodiment of the present invention, in order to increase vagal tone while at the same time minimizing or preventing the heart-rate-lowering effects of the stimulation, control unit 32 applies the signals to the parasympathetic site as a burst of pulses during each cardiac cycle, with one or more of the following parameters:

Timing of the stimulation: delivery of the burst of pulses begins after a variable delay following each P-wave, the length of the delay equal to between about two-thirds and about 90% of the length of the subject's cardiac cycle. Such a delay is typically calculated on a real-time basis by continuously measuring the length of the subject's cardiac cycle.

Pulse duration: each pulse typically has a duration of between about 200 microseconds and about 2.5 milliseconds for some applications, or, for other applications, between about 2.5 milliseconds and about 5 milliseconds.

Pulse amplitude: the pulses are typically applied with an amplitude of between about 0.5 and about 5 mA, e.g., about 1 mA.

Pulse repetition interval (PRI): the pulses within the burst of pulses typically have a PRI (the time from the initiation of a pulse to the initiation of the following pulse) of, on average, at least 20 ms, such as at least 30 ms, e.g., at least 50 ms or at least 75 ms; alternatively, the PRI may be between about 2 and about 10 milliseconds, e.g., about 2.5 milliseconds.

Pulse period: the burst of pulses typically has a total duration of between about 0.2 and about 40 milliseconds, e.g., about 1 millisecond.

Pulses per trigger (PPT): the burst of pulses typically contains between about 1 and about 10 pulses, e.g., about 2 pulses.

Site: for some applications, the left vagus nerve is stimulated in order to minimize the heart-rate-lowering effects of vagal stimulation.

Duty cycle: stimulation is typically applied only once every several heartbeats, or once per heartbeat, when a stronger effect is desired.

On/off status: for some applications, stimulation is always "on", i.e., constantly applied (in which case, parameters closer to the lower ends of the ranges above are typically used). For other applications, on/off cycles vary between a few seconds to several dozens of seconds, e.g., "on" for about 36 seconds, "off" for about 120 seconds, "on" for about 3 seconds, "off" for about 9 seconds.

For example, stimulation may be applied to a subject having a heart rate of 60 BPM, with the intention of minimally reducing the subject's heart rate. The burst of pulses may be delivered beginning about 750 milliseconds after each R-wave of the subject. The stimulation may be applied with one pulse per trigger (PPT), and having an amplitude of 1 mA. The stimulation may be cycled between "on" and "off" periods, with each "on" period having a duration of about two seconds, i.e., two heart beats, and each "off" period having a duration of about 4 seconds.

In an embodiment of the present invention, control unit 32 is configured to sense a heart rate of the subject, and to apply the stimulation with minimal-heart-rate-reducing parameters only when the sensed heart rate is below a threshold rate. For some applications, the threshold is a normal heart rate for the subject, or a percentage of the normal heart rate, e.g., between about 80% and about 100%, such as between about 80% and about 95%, or between about 80% and about 120%, e.g., between about 95% and about 105%, such as about 100%. The normal heart rate of the subject may be sensed by control unit 32, or entered into the control unit by a medical professional. Alternatively, the threshold is a normal heart rate for typical subjects, such as between about 50 and about 80 BPM, or a percentage of the normal heart rate, e.g., between about 80% and about 100%, such as between about 80% and about 95%, or between about 80% and about 120%, e.g., between about 95% and about 105%, such as about 100%. Applying the stimulation only when the sensed heart rate is below the threshold rate further reduces any heart-rate-lowering effects of the stimulation, because the stimulation has less effect on heart rate at lower heart rates. Furthermore, it is sometimes undesirable to apply the stimulation when the subject's heart rate is elevated, either because of normal causes, such as exercise, or because of pathological causes, such as ventricular or atrial tachycardia.

Alternatively or additionally, the control unit drives pacemaker 42 to pace the heart, so as to prevent any heart-rate lowering effects of stimulation. Typically, the control unit paces the heart at a rate that is similar to the rate when the device is in "off" mode. Control unit 32 then applies the stimulation, typically using the typical stimulation parameters described hereinabove. This stimulation generally does not lower the heart rate, because of the pacemaker pacing. For some applications, control unit 32 applies the signals, and senses the heart rate after applying the signals. The control unit drives pacemaker 42 to pace the heart if the sensed heart rate falls below a threshold heart rate. The threshold heart rate is typically equal to a heart rate of the subject prior to commencing the stimulation, for example, as sensed by control unit 32. The control unit thus typically maintains the heart rate at a rate above a bradycardia threshold rate, unlike conventional pacemakers which are typically configured to pace the heart only when the rate falls below a bradycardia threshold rate. Upon termination of stimulation, control unit 32 typically drives pacemaker 42 to continue pacing the heart for a period typically having a duration between about 0 and about 30 seconds, such as about 5 seconds.

In an embodiment of the present invention, control unit 32 drives pacemaker 42 to pace the heart, and configures the signals applied to the vagal or other parasympathetic site using the typical stimulation parameters described hereinabove. For some applications, the higher ends of the ranges of values for one or more of these parameters are applied. The use of the pacemaker generally prevents any heart-rate-lowering effects of such stimulation.

In an embodiment of the present invention, control unit 32 applies minimal-heart-rate-lowering stimulation using a feedback loop. The control unit calculates an average heart rate (ventricular and/or atrial rate) of the subject. The control unit then applies signals to vagus nerve 24 or another of the parasympathetic sites listed hereinabove, using the minimal heart rate reduction parameters described hereinabove. During such stimulation, the control unit substantially continuously monitors the resulting heart rate. If the heart rate declines by more than a certain percentage (e.g., by more than about 5%, such as from 100 BPM to 90 BPM), the control unit adjusts the stimulation parameters in order to further minimize the heart-rate-lowering effect of the stimulation. For example, the control unit may adjust the stimulation parameters by reducing the amplitude of the stimulation, changing the timing of the stimulation, reducing the frequency of the stimulation, reducing the duration of each pulse, and/or reducing the duration of the stimulation period.

In an embodiment of the present invention, control unit 32 is configured to apply signals to vagus nerve 24 of subject 30 or another of the parasympathetic sites listed hereinabove, and to configure the signals to inhibit propagation of naturally-generated efferent action potentials in the vagus nerve. Typically, the signals are additionally configured to inhibit no more than about 10% of naturally-generated afferent action potentials traveling through the vagus nerve. It is hypothesized by the inventors that such inhibition is useful for treating AF, typically by enhancing drug efficacy, and for preventing bradycardia.

Experimental evidence supporting the efficacy of some embodiments of the present invention is presented in above-mentioned U.S. patent application Ser. No. 10/866,601 with reference to FIGS. 6-10B thereof, which, as mentioned above, is incorporated herein by reference.

In an embodiment of the present invention, apparatus 20 is adapted to be used prior to, during, and/or following a clinical procedure. In addition to configuring the stimulation to reduce the likelihood of the occurrence of an episode of AF, for some applications control unit 32 configures the current to reduce a potential immune-mediated response to the procedure. Such a reduction generally promotes healing after the procedure. (See Borovikova L V et al. cited hereinabove, which describe an anti-inflammatory cholinergic pathway that may mediate this reduction in immune-related response.) When the procedure is heart-related, the stimulation additionally typically reduces mechanical stress by lowering heart rate and pressures, reduces heart rate, and/or improves coronary blood flow.

For some applications, the stimulation commences after the conclusion of the procedure. For some applications, the stimulation commences prior to the commencement of the procedure. Alternatively, the stimulation commences during the procedure. Further alternatively, the stimulation is applied before and after the procedure, but not during the procedure.

For some applications, the clinical procedure is selected from one of the following:

coronary artery bypass graft (CABG) surgery. In addition to the benefits of stimulation described above, vagal tone was shown by Cumming J E et al. (cited hereinabove) to be effective in reducing the likelihood of postoperative atrial fibrillation (AF), increasing the likelihood that the graft will stay in place, reducing the likelihood of graft failure (e.g., via stenosis), improving healing from the surgery, and/or reducing pain associated with the surgery. It is hypothesized by the inventors that such a reduction in the likelihood of postoperative AF is due, at least in part, to the mechanical stress reduction and rhythmic vagal activity promoted by vagal or other parasympathetic stimulation. For some applications, the stimulation is applied for between 1 and 7 days after the CABG surgery, intermittently or continuously.

valve replacement surgery. In addition to the benefits of stimulation described above, stimulation generally reduces the likelihood of postoperative AF, promotes healing of the heart, and reduces the likelihood of other conductance abnormalities.

heart transplantation. In addition to the benefits of stimulation described above, stimulation generally reduces the likelihood of rejection of the transplanted heart. For some applications, stimulation is applied on a short-term basis, e.g., for less than about 7 days before and/or 7 days after the heart transplantation. Alternatively, stimulation is applied long-term, e.g., for more than about 2 weeks before and/or 2 weeks after the procedure.

percutaneous transluminal coronary angioplasty (PTCA) and/or stenting procedures. In addition to the benefits of stimulation described above, stimulation generally reduces the likelihood of restenosis, which is believed to be at least in part immune-mediated. In addition, stimulation induces coronary dilation, which generally reduces the likelihood of restenosis.

carotid endarterectomy. In addition to the benefits of stimulation described above, stimulation generally reduces the likelihood of restenosis, which is believed to be at least in part immune-mediated.

other bypass surgery. In addition to the benefits of stimulation described above, stimulation generally reduces the likelihood of restenosis in the grafted bypass (natural or artificial).

In an embodiment of the present invention, control unit 32 is configured to operate in one of the following modes:

stimulation is applied using fixed programmable parameters, i.e., not in response to any feedback, target heart rate, or target heart rate range. These parameters may be externally updated from time to time, for example by a physician;

stimulation is not applied when the heart rate of the subject is lower than the low end of the normal range of a heart rate of the subject and/or of a typical human subject;

stimulation is not applied when the heart rate of the subject is lower than a threshold value equal to the current low end of the range of the heart rate of the subject, i.e., the threshold value is variable over time as the low end generally decreases as a result of chronic stimulation treatment;

stimulation is applied only when the heart rate of the subject is within the normal of range of a heart rate of the subject and/or of a typical human subjects; or stimulation is applied only when the heart rate of the subject is greater than a programmable threshold value, such as a rate higher than a normal rate of the subject and/or a normal rate of a typical human subject. This mode generally removes peaks in heart rate.

For many of the applications of parasympathetic stimulation described herein, electrode device 22 typically comprises one or more electrodes, such as monopolar, bipolar or tripolar electrodes. Electrode device 22 is typically placed: (a) around vagus nerve 24, (b) around vagus nerve 24 and the carotid artery (configuration not shown), or (c) inside the carotid artery in a position suitable for vagal stimulation (not shown). Depending on the particular application, one or more electrode devices 22 may be positioned to stimulate the left or right vagus nerve, either above or below the cardiac branch bifurcation. For some applications, the electrodes comprise cuff electrodes, ring electrodes, and/or point electrodes. Typically, the electrodes stimulate the nerve without coming in direct contact therewith, by applying an electrical field to the nerve. Alternatively, the electrodes stimulate the nerve by coming in direct contact therewith. Control unit 32 typically configures the signals to induce the propagation of efferent nerve impulses towards heart 28.

In some embodiments of the present invention, when configuring vagal stimulation to induce the propagation of efferent nerve impulses towards heart 28, control unit 32 drives electrode device 22 to (a) apply signals to induce the propagation of efferent nerve impulses towards heart 28, and (b) suppress artificially-induced afferent nerve impulses towards a brain 35 of the subject (FIG. 1), in order to minimize unintended side effects of the signal application.

Figure 2A:
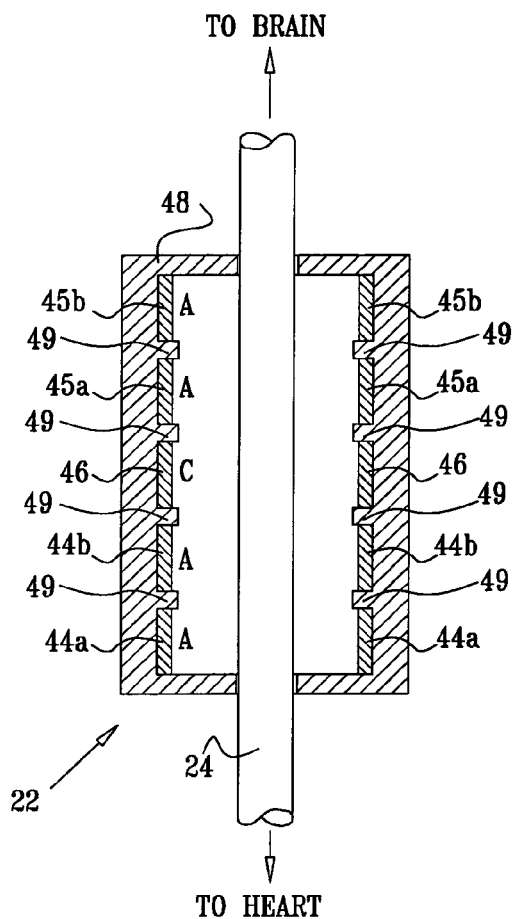
FIG. 2A is a simplified cross-sectional illustration of a multipolar electrode device applied to a vagus nerve, in accordance with an embodiment of the present invention.

FIG. 2A is a simplified cross-sectional illustration of a generally-cylindrical electrode device 22 applied to vagus nerve 24, in accordance with an embodiment of the present invention. Electrode device 22 comprises a central cathode 46 for applying a negative current ("cathodic current") in order to stimulate vagus nerve 24, as described below. Electrode device 22 additionally comprises a set of one or more anodes 44 (44a, 44b, herein: "efferent anode set 44"), placed between cathode 46 and the edge of electrode device 22 closer to heart 28 (the "efferent edge"). Efferent anode set 44 applies a positive current ("efferent anodal current") to vagus nerve 24, for blocking action potential conduction in vagus nerve 24 induced by the cathodic current, as described below. Typically, electrode device 22 comprises an additional set of one or more anodes 45 (45a, 45b, herein: "afferent anode set 45"), placed between cathode 46 and the edge of electrode device 22 closer to brain 35. Afferent anode set 45 applies a positive current ("afferent anodal current") to vagus nerve 24, in order to block propagation of action potentials in the direction of the brain during application of the cathodic current.

For some applications, the one or more anodes of efferent anode set 44 are directly electrically coupled to the one or more anodes of afferent anode set 45, such as by a common wire or shorted wires providing current to both anode sets, substantially without any intermediary elements. Typically, the sizes of the anodes and/or distances of the various anodes from the nerve are regulated so as to produce desired ratios of currents delivered through the various anodes. In these applications, central cathode 46 is typically placed closer to one of the anode sets than to the other, for example, so as to induce asymmetric stimulation (i.e., not necessarily unidirectional in all fibers) between the two sides of the electrode device. The closer anode set typically induces a stronger blockade of the cathodic stimulation.

Cathode 46 and anode sets 44 and 45 (collectively, "electrodes") are typically mounted in a housing such as an electrically-insulating cuff 48 and separated from one another by insulating elements such as protrusions 49 of the cuff. Typically, the width of the electrodes is between about 0.5 and about 2 millimeters, or is equal to approximately one-half the radius of the vagus nerve. The electrodes are typically recessed so as not to come in direct contact with vagus nerve 24. For some applications, such recessing enables the electrodes to achieve generally uniform field distributions of the generated currents and/or generally uniform values of the activation function defined by the electric potential field in the vicinity of vagus nerve 24. Alternatively or additionally, protrusions 49 allow vagus nerve 24 to swell into the canals defined by the protrusions, while still holding the vagus nerve centered within cuff 48 and maintaining a rigid electrode geometry. For some applications, cuff 48 comprises additional recesses separated by protrusions, which recesses do not contain active electrodes. Such additional recesses accommodate swelling of vagus nerve 24 without increasing the contact area between the vagus nerve and the electrodes. For some applications, the distance between the electrodes and the axis of the vagus nerve is between about 1 and about 4 millimeters, and is greater than the closest distance from the ends of the protrusions to the axis of the vagus nerve. Typically, protrusions 49 are relatively short (as shown). The distance between the ends of protrusions 49 and the center of the vagus nerve is typically between about 1 and 3 millimeters. (Generally, the diameter of the vagus nerve is between about 2 and 3 millimeters.) Alternatively, for some applications, protrusions 49 are longer and/or the electrodes are placed closer to the vagus nerve in order to reduce the energy consumption of electrode device 22.

In an embodiment of the present invention, efferent anode set 44 comprises a plurality of anodes 44, typically two anodes 44a and 44b, spaced approximately 0.5 to 2.0 millimeters apart. Application of the efferent anodal current in appropriate ratios from the plurality of anodes generally minimizes the "virtual cathode effect," whereby application of too large an anodal current stimulates rather than blocks fibers. In an embodiment, anode 44a applies a current with an amplitude equal to about 0.5 to about 5 mA (typically one-third of the amplitude of the current applied by anode 44b).

Anode 44a is typically positioned in cuff 48 to apply current at the location on vagus nerve 24 where the virtual cathode effect is maximally generated by anode 44b. For applications in which the blocking current through anode 44b is expected to vary substantially, efferent anode set 44 typically comprises a plurality of virtual-cathode-inhibiting anodes 44a, one or more of which is activated at any time based on the expected magnitude and location of the virtual cathode effect.

Likewise, afferent anode set 45 typically comprises a plurality of anodes 45, typically two anodes 45a and 45b, in order to minimize the virtual cathode effect in the direction of the brain. In certain electrode configurations, cathode 46 comprises a plurality of cathodes in order to minimize the "virtual anode effect," which is analogous to the virtual cathode effect.

Figure 2B:
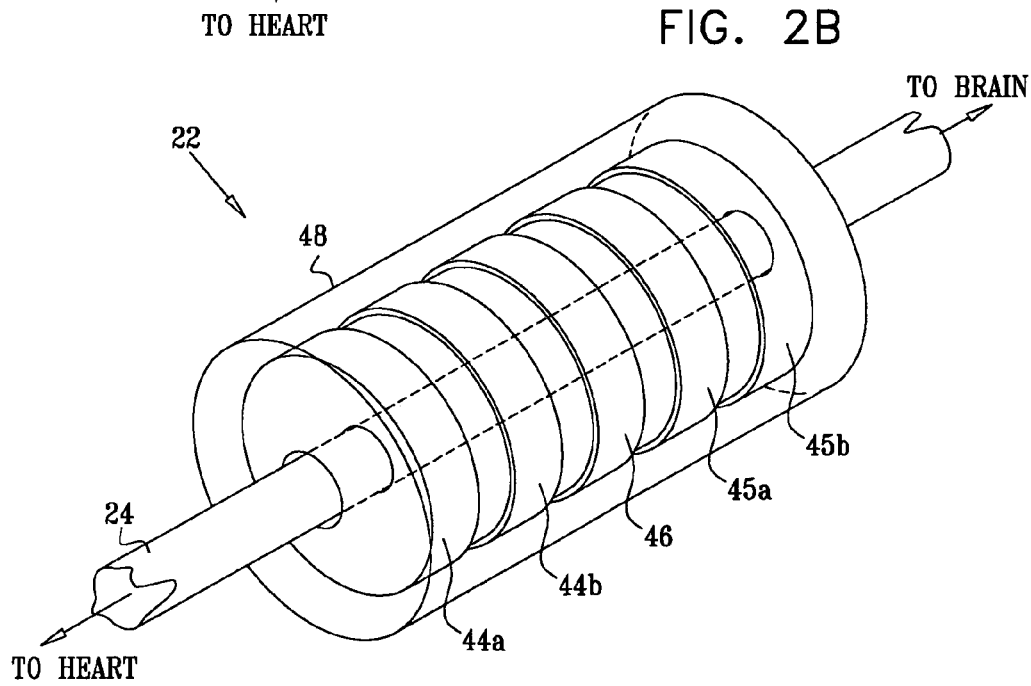
FIG. 2B is a simplified perspective illustration of the electrode device of FIG. 2A, in accordance with an embodiment of the present invention.

FIG. 2B is a simplified perspective illustration of electrode device 22, in accordance with an embodiment of the present invention. When applied to vagus nerve 24, electrode device 22 typically encompasses the nerve. As described, control unit 32 typically drives electrode device 22 to (a) apply signals to vagus nerve 24 in order to induce the propagation of efferent action potentials towards heart 28, and (b) suppress artificially-induced afferent action potentials towards brain 35. The electrodes typically comprise ring electrodes adapted to apply a generally uniform current around the circumference of the nerve, as best shown in FIG. 2B.

FIG. 3 is a simplified perspective illustration of a multipolar point electrode device 140 applied to vagus nerve 24, in accordance with an embodiment of the present invention. In this embodiment, anodes 144a and 144b and a cathode 146 typically comprise point electrodes (typically 2 to 100), fixed inside an insulating cuff 148 and arranged around vagus nerve 24 so as to selectively stimulate nerve fibers according to their positions inside the nerve. In this case, techniques described in the above-cited articles by Grill et al., Goodall et al., and/or Veraart et al. may be used. The point electrodes typically have a surface area between about 0.01 mm2 and 1 mm2. In some applications, the point electrodes are in contact with vagus nerve 24, as shown, while in other applications the point electrodes are recessed in cuff 148, so as not to come in direct contact with vagus nerve 24, similar to the recessed ring electrode arrangement described above with reference to FIG. 2A. For some applications, one or more of the electrodes, such as cathode 146 or anode 144a, comprise a ring electrode, as described with reference to FIG. 2B, such that electrode device 140 comprises both ring electrode(s) and point electrodes (configuration not shown). Additionally, electrode device 22 optionally comprises an afferent anode set (positioned like anodes 45a and 45b in FIG. 2A), the anodes of which comprise point electrodes and/or ring electrodes.

Alternatively, ordinary, non-cuff electrodes are used, such as when the electrodes are placed on the epicardial fat pads instead of on the vagus nerve.

Figure 4:
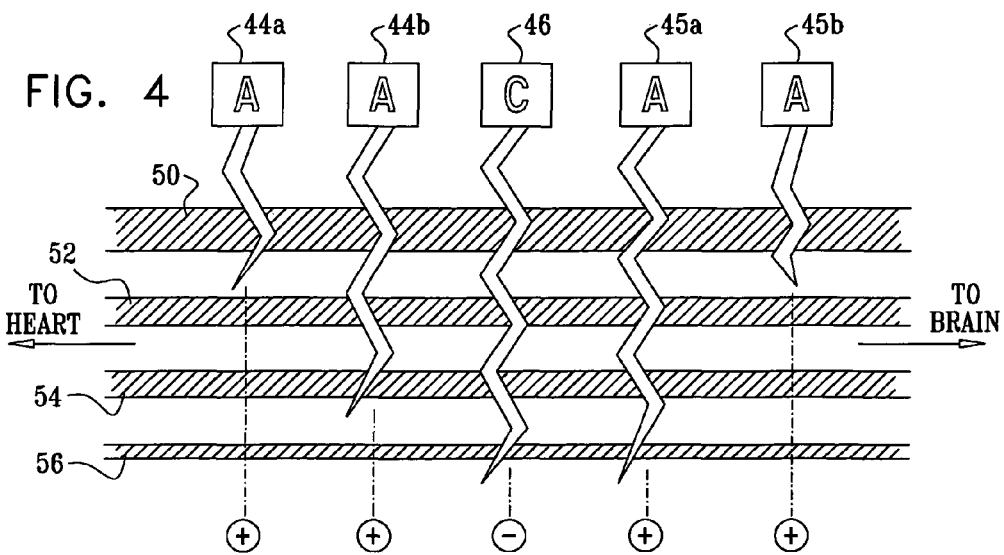
FIG. 4 is a conceptual illustration of the application of current to a vagus nerve, in accordance with an embodiment of the present invention.

FIG. 4 is a conceptual illustration of the application of current to vagus nerve 24 in order to achieve smaller-to-larger diameter fiber recruitment, in accordance with an embodiment of the present invention. When inducing efferent action potentials towards heart 28, control unit 32 drives electrode device 22 to selectively recruit nerve fibers beginning with smaller-diameter fibers and to progressively recruit larger-diameter fibers as the desired stimulation level increases. This smaller-to-larger diameter recruitment order mimics the body's natural order of recruitment.

Typically, in order to achieve this recruitment order, the control unit stimulates myelinated fibers essentially of all diameters using cathodic current from cathode 46, while simultaneously inhibiting fibers in a larger-to-smaller diameter order using efferent anodal current from efferent anode set 44. For example, FIG. 4 illustrates the recruitment of a single, smallest nerve fiber 56, without the recruitment of any larger fibers 50, 52 and 54. The depolarizations generated by cathode 46 stimulate all of the nerve fibers shown, producing action potentials in both directions along all the nerve fibers. Efferent anode set 44 generates a hyperpolarization effect sufficiently strong to block only the three largest nerve fibers 50, 52 and 54, but not fiber 56. This blocking order of larger-to-smaller diameter fibers is achieved because larger nerve fibers are inhibited by weaker anodal currents than are smaller nerve fibers. Stronger anodal currents inhibit progressively smaller nerve fibers. When the action potentials induced by cathode 46 in larger fibers 50, 52 and 54 reach the hyperpolarized region in the larger fibers adjacent to efferent anode set 44, these action potentials are blocked. On the other hand, the action potentials induced by cathode 46 in smallest fiber 56 are not blocked, and continue traveling unimpeded toward heart 28. Anode pole 44a is shown generating less current than anode pole 44b in order to minimize the virtual cathode effect in the direction of the heart, as described above.

When desired, in order to increase the parasympathetic stimulation delivered to the heart, the number of fibers not blocked is progressively increased by decreasing the amplitude of the current applied by efferent anode set 44. The action potentials induced by cathode 46 in the fibers now not blocked travel unimpeded towards the heart. As a result, the parasympathetic stimulation delivered to the heart is progressively increased in a smaller-to-larger diameter fiber order, mimicking the body's natural method of increasing stimulation. Alternatively or additionally, in order to increase the number of fibers stimulated, while simultaneously decreasing the average diameter of fibers stimulated, the amplitudes of the currents applied by cathode 46 and efferent anode set 44 are both increased (thereby increasing both the number of fibers stimulated and number of fibers blocked). In addition, for any given number of fibers stimulated (and not blocked), the amount of stimulation delivered to the heart can be increased by increasing the PPT, frequency, and/or pulse width of the current applied to vagus nerve 24.

In order to suppress artificially-induced afferent action potentials from traveling towards the brain in response to the cathodic stimulation, control unit 32 typically drives electrode device 22 to inhibit fibers 50, 52, 54 and 56 using afferent anodal current from afferent anode set 45. When the afferent-directed action potentials induced by cathode 46 in all of the fibers reach the hyperpolarized region in all of the fibers adjacent to afferent anode set 45, the action potentials are blocked. Blocking these afferent action potentials generally minimizes any unintended side effects, such as undesired or counterproductive feedback to the brain, that might be caused by these action potentials. Anode 45b is shown generating less current than anode 45a in order to minimize the virtual cathode effect in the direction of the brain, as described above.

In an embodiment of the present invention, the amplitude of the cathodic current applied in the vicinity of the vagus nerve is between about 2 mA and about 10 mA. Such a current is typically used in embodiments that employ techniques for achieving generally uniform stimulation of the vagus nerve, i.e., stimulation in which the stimulation applied to fibers on or near the surface of the vagus nerve is generally no more than about 400% greater than stimulation applied to fibers situated more deeply in the nerve. This corresponds to stimulation in which the value of the activation function at fibers on or near the surface of the vagus nerve is generally no more than about four times greater than the value of the activation function at fibers situated more deeply in the nerve. For example, as described hereinabove with reference to FIG. 2A, the electrodes may be recessed so as not to come in direct contact with vagus nerve 24, in order to achieve generally uniform values of the activation function. Typically, but not necessarily, embodiments using approximately 5 mA of cathodic current have the various electrodes disposed approximately 0.5 to 2.5 mm from the axis of the vagus nerve. Alternatively, larger cathodic currents (e.g., 10-30 mA) are used in combination with electrode distances from the axis of the vagus nerve of greater than 2.5 mm (e.g., 2.5-4.0 mm), so as to achieve an even greater level of uniformity of stimulation of fibers in the vagus nerve.

In an embodiment of the present invention, the cathodic current is applied by cathode 46 with an amplitude sufficient to induce action potentials in large- and medium-diameter fibers 50, 52, and 54 (e.g., A- and B-fibers), but insufficient to induce action potentials in small-diameter fibers 56 (e.g., C-fibers). Simultaneously, an anodal current is applied by anode 44b in order to inhibit action potentials induced by the cathodic current in the large-diameter fibers (e.g., A-fibers). This combination of cathodic and anodal current generally results in the stimulation of medium-diameter fibers (e.g., B-fibers) only. At the same time, a portion of the afferent action potentials induced by the cathodic current are blocked by anode 45a, as described above. Alternatively, the afferent anodal current is configured to not fully block afferent action potentials, or is simply not applied. In these cases, artificial afferent action potentials are nevertheless generally not generated in C-fibers, because the applied cathodic current is not strong enough to generate action potentials in these fibers.

These techniques for efferent stimulation of only B-fibers are typically used in combination with techniques described hereinabove for achieving generally uniform stimulation of the vagus nerve. Such generally uniform stimulation enables the use of a cathodic current sufficiently weak to avoid stimulation of C-fibers near the surface of the nerve, while still sufficiently strong to stimulate B-fibers, including B-fibers situated more deeply in the nerve, i.e., near the center of the nerve. For some applications, when employing such techniques for achieving generally uniform stimulation of the vagus nerve, the amplitude of the cathodic current applied by cathode 46 may be between about 3 and about 10 mA, and the amplitude of the anodal current applied by anode 44b may be between about 1 and about 7 mA.

For some applications, control unit 32 is adapted to receive feedback from one or more of the electrodes in electrode device 22, and to regulate the signals applied to the electrode device responsive thereto. For example, control unit 32 may analyze amplitudes of various peaks in a compound action potential (CAP) signal recorded by the electrodes, in order to determine a relative proportion of stimulated larger fibers (having faster conduction velocities) to smaller fibers (having slower conduction velocities). Alternatively or additionally, control unit 32 analyzes an area of the CAP, in order to determine an overall effect of the stimulation. In an embodiment, the feedback is received by electrodes other than those used to apply signals to the nerve.

Figure 5:
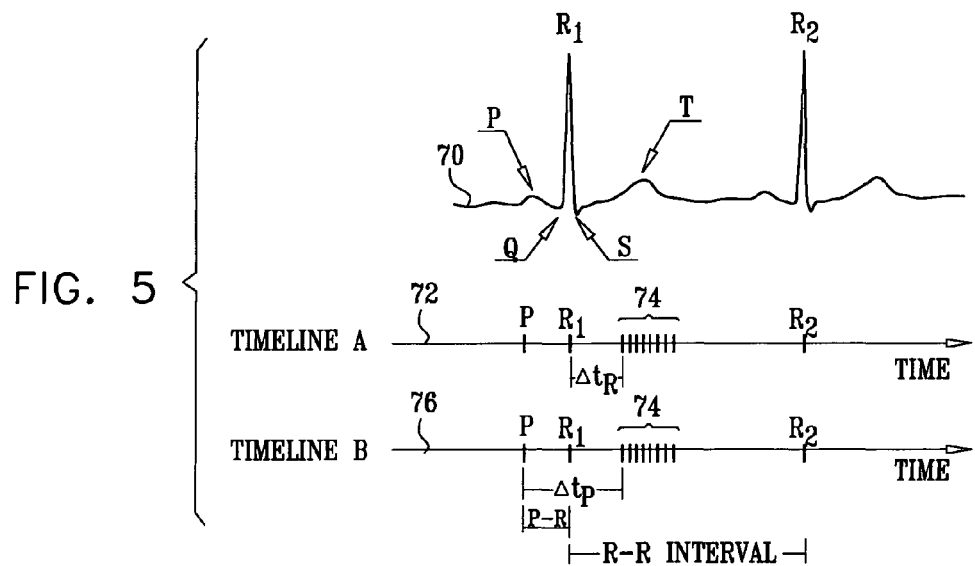
FIG. 5 is a simplified illustration of an electrocardiogram (ECG) recording and of example timelines showing the timing of the application of a series of stimulation pulses, in accordance with an embodiment of the present invention.

FIG. 5 is a simplified illustration of an ECG recording 70 and example timelines 72 and 76 showing the timing of the application of a burst of stimulation pulses 74, in accordance with an embodiment of the present invention. The application of the burst of pulses in each cardiac cycle typically commences after a variable delay after a detected R-wave, P-wave, or other feature of an ECG. For some applications, other parameters of the applied burst of pulses are also varied in real time. Such other parameters include amplitude, pulses per trigger (PPT), pulse duration, and PRI. For some applications, the delay and/or one or more of the other parameters are calculated in real time using a function, the inputs of which include one or more pre-programmed but updateable constants and one or more sensed parameters, such as the R-R interval between cardiac cycles and/or the P-R interval.

The variable delay before applying pulse burst 74 in each cardiac cycle can be measured from a number of sensed physiological parameters ("initiation physiological parameters"), including sensed points in the cardiac cycle, including P-, Q-, R-, S- and T-waves. Typically the delay is measured from the P-wave, which indicates atrial contraction. Alternatively, the delay is measured from the R-wave, particularly when the P-wave is not easily detected. Timeline A 72 and Timeline B 76 show the delays, $dt_R$ and $dt_P$ measured from R and P, respectively.

In an embodiment, a lookup table of parameters, such as delays (e.g., dt) and/or other parameters, is used to determine in real time the appropriate parameters for each application of pulses, based on the one or more sensed parameters, and/or based on a predetermined sequence stored in the lookup table.

Optionally, the stimulation applied by stimulation apparatus 20 is applied in conjunction with or separately from stimulation of sympathetic nerves innervating the heart. For example, inhibition described herein and/or periods of non-stimulation described herein may be replaced or supplemented by excitation of sympathetic nerves. Such sympathetic stimulation can be applied using techniques of smaller-to-larger diameter fiber recruitment, as described herein, or other nerve stimulation techniques known in the art. For some applications, vagal or other parasympathetic stimulation is applied in conjunction with stimulation of sympathetic nerves in order to increase vagal tone while minimizing the heart-rate-lowering effect of the parasympathetic stimulation.

Alternatively or additionally, the techniques of smaller-to-larger diameter fiber recruitment are applied in conjunction with methods and apparatus described in one or more of the patents, patent applications, articles and books cited herein.

Figure 6:
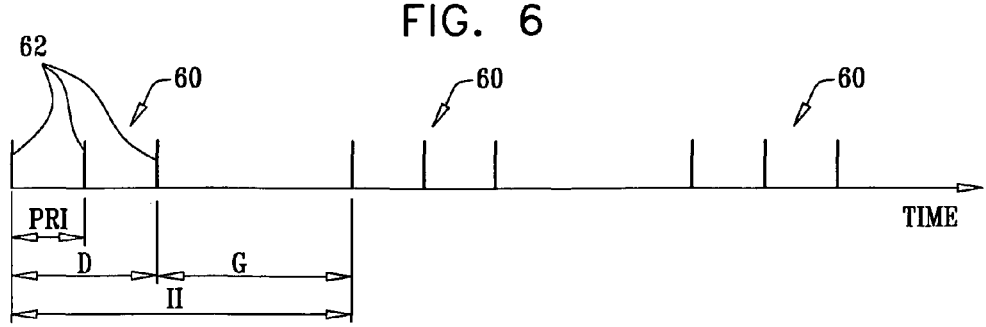
FIG. 6 is a schematic illustration of a series of bursts, in accordance with an embodiment of the present invention.

Reference is made to FIG. 6, which is a schematic illustration of a series of bursts 60, in accordance with an embodiment of the present invention. Control unit 32 is configured to drive electrode device 26 to apply stimulation, such as for reducing the risk of AF, as described herein, in the series of bursts 60, at least one of which bursts includes a plurality of pulses 62, such as at least three pulses 62. Control unit 32 configures:

(a) a pulse repetition interval (PRI) within each of multi-pulse bursts 60 (i.e., the time from the initiation of a pulse to the initiation of the following pulse within the same burst) to be on average at least 20 ms, such as at least 30 ms, e.g., at least 50 ms or at least 75 ms, and (b) an interburst interval (II) (i.e., the time from the initiation of a burst to the initiation of the following burst) to be at least a multiple M times the burst duration D. Multiple M is typically at least 1.5 times the burst duration D, such as at least 2 times the burst duration, e.g., at least 3 or 4 times the burst duration. (Burst duration D is the time from the initiation of the first pulse within a burst to the conclusion of the last pulse within the burst.)

In other words, burst duration D is less than a percentage P of interburst interval II, such as less than 75%, e.g., less than 67%, 50%, or 33% of the interval. For some applications, the PRI varies within a given burst, in which case the control unit sets the PRI to be on average at least 20 ms, such as at least 30 ms, e.g., at least 50 ms or at least 75 ms. For other applications, the PRI does not vary within a given burst (it being understood that for these applications, the "average PRI" and the PRI "on average," including as used in the claims, is equivalent to the PRI; in other words, the terms "average PRI" and the PRI "on average" include within their scope both (a) embodiments with a constant PRI within a given burst, and (b) embodiments with a PRI that varies within a given burst).

Typically, each burst 60 includes between two and 14 pulses 62, e.g., between two and six pulses, and the pulse duration (or average pulse duration) is between about 0.1 and about 4 ms, such as between about 100 microseconds and about 2.5 ms, e.g., about 1 ms. Typically, control unit 32 sets the interburst interval II to be less than 10 seconds. For some applications, control unit 32 is configured to set the interburst interval II to be between 400 ms and 1500 ms, such as between 750 ms and 1500 ms. Typically, control unit 32 sets an interburst gap G between a conclusion of each burst 60 and an initiation of the following burst 60 to have a duration greater than the PRI. For some applications, the duration of the interburst gap G is at least 1.5 times the PRI, such as at least 2 times the PRI, at least 3 times the PRI, or at least 4 times the PRI.

Although the control unit typically withholds applying current during the periods between bursts and between pulses, it is to be understood that the scope of the present invention includes applying a low level of current during such periods, such as less than 50% of the current applied during the "on" periods, e.g., less than 20% or less than 5%. Such a low level of current is hypothesized to have a different, significantly lower, or a minimal physiological effect on the subject. For some applications, control unit 32 is configured to apply an interburst current during at least a portion of interburst gap G, and to set the interburst current on average to be less than 50% (e.g., less than 20%) of the current applied on average during the burst immediately preceding the gap. For some applications, control unit 32 is configured to apply an interpulse current to the site during at least a portion of the time that the pulses of bursts 60 are not being applied, and to set the interpulse current on average to be less than 50% (e.g., less than 20%) of the current applied on average during bursts 60.

For some applications, the control unit is configured to synchronize the bursts with a feature of the cardiac cycle of the subject. For example, each of the bursts may commence after a delay after a detected R-wave, P-wave, or other feature of an ECG. For these applications, one burst is typically applied per heart beat, so that the interburst interval II equals the R-R interval, or a sum of one or more sequential R-R intervals of the subject. Alternatively, for some applications, the control unit is configured to synchronize the bursts with other physiological activity of the subject, such as respiration, muscle contractions, or spontaneous nerve activity.

In an embodiment of the present invention, the control unit sets the PRI to at least 75% of a maximum possible PRI for a given interburst interval II (such as the R-R interval of the subject), desired percentage P, and desired PPT. For some applications, the following equation is used to determine the maximum possible PRI:

$$PRI = II*P/(PPT-1) \quad \text{(Equation 1)}$$

For example, if the II is 900 ms, percentage P is 33.3%, and the desired PPT is 4 pulses, the maximum possible PRI would be 900 ms*33.3%/(4−1)=100 ms, and the control unit would set the actual PRI to be at least 75 ms. For some applications, control unit 32 uses this equation to determine the PRI, such as in real time or periodically, while for other applications this equation is used to produce a look-up table which is stored in the control unit. For still other applications, this equation is used to configure the control unit. For some applications, multiple M is a constant, which is stored in control unit 32, while for other applications, control unit 32 adjusts M during operation, such as responsively to one or more sensed physiological values, or based on the time of day, for example. It is noted that Equation 1 assumes that the pulse width of the pulses does not contribute meaningfully to burst duration D. Modifications to Equation 1 to accommodate longer pulse widths will be evident to those skilled in the art.

For some applications, when using Equation 1, a maximum value is set for the PRI, such as between 175 and 225, e.g., about 200, and the PRI is not allowed to exceed this maximum value regardless of the result of Equation 1.

Reference is made to FIG. 7, which is a schematic illustration of a stimulation regimen, in accordance with an embodiment of the present invention. Control unit 32 is configured to apply the stimulation, such as for reducing the risk of AF, as described herein, during "on" periods 100 alternating with "off" periods 102, during which no stimulation is applied (each set of a single "on" period followed by a single "off" period is referred to hereinbelow as a "cycle" 104). Typically, each of "on" periods 100 has an "on" duration equal to at least 1 second (e.g., between 1 and 10 seconds), and each of "off" periods 102 has an "off" duration equal to at least 50% of the "on" duration, e.g., at least 100% or 200% of the "on" duration. Control unit 32 is further configured to apply such intermittent stimulation during stimulation periods 110 alternating with rest periods 112, during which no stimulation is applied. Each of rest periods 102 typically has a duration equal to at least the duration of one cycle 104, e.g., between one and 50 cycles, such as between two and four cycles, and each of stimulation periods 110 typically has a duration equal to at least 5 times the duration of one of rest periods 112, such as at least 10 times, e.g., at least 15 times. For example, each of stimulation periods 110 may have a duration of at least 30 cycles, e.g., at least 60 cycles or at least 120 cycles, and no greater than 2400 cycles, e.g., no greater than 1200 cycles. Alternatively, the duration of the stimulation and rest periods are expressed in units of time, and each of the rest periods has a duration of at least 30 seconds, e.g., such as at least one minute, at least two minutes, at least five minutes, or at least 25 minutes, and each of the stimulation periods has a duration of at least 10 minutes, e.g., at least 30 minutes, such as at least one hour, and less than 12 hours, e.g., less than six hours, such as less than two hours.

For some applications, low stimulation periods are used in place of "off" periods 102. During these low stimulation periods, the control unit sets the average current applied to be less than 50% of the average current applied during the "on" periods, such as less than 20% or less than 5%. Similarly, for some applications, the control unit is configured to apply a low level of current during the rest periods, rather than no current. For example, the control unit may set the average current applied during the rest periods to be less than 50% of the average current applied during the "on" periods, such as less than 20% or less than 5%. As used in the present application, including in the claims, the "average current" or "current applied on average" during a given period means the total charge applied during the period (which equals the integral of the current over the period, and may be measured, for example, in coulombs) divided by the duration of the period, such that the average current may be expressed in mA, for example.

For some applications, these rest period stimulation techniques are combined with the extended PRI techniques described hereinabove with reference to FIG. 6.

Reference is made to FIG. 8, which is a schematic illustration of a stimulation regimen, in accordance with an embodiment of the present invention. In this embodiment, control unit 32 is configured to apply stimulation, such as for reducing the risk of AF, as described herein, in a series of bursts 200, each of which includes one or more pulses 202 (pulses per trigger, or PPT). The control unit is configured to apply the stimulation intermittently during "on" periods 204 alternating with "off" periods 206, during which no stimulation is applied. Each "on" period 204 includes at least 3 bursts 200, such as at least 10 bursts 200, and typically has a duration of between 3 and 20 seconds. At the commencement of each "on" period 204, control unit 32 ramps up the PPT of successive bursts 200, and at the conclusion of each "on" period 204, the control unit ramps down the PPT of successive bursts 200. For example, the first four bursts of an "on" period 204 may have respective PPTs of 1, 2, 3, and 3, or 1, 2, 3, and 4, and the last four bursts of an "on" period 204 may have respective PPTs of 3, 3, 2, and 1, or 4, 3, 2, and 1.

Alternatively, rather than increase or decrease the PPT by 1 in successive bursts, control unit 32 increases or decreases the PPT more gradually, such as by 1 in less than every successive burst, e.g., the first bursts of an "on" period may have respective PPTs of 1, 1, 2, 2, 3, 3, and 4, and the last bursts of an "on" period may have respective PPTs of 4, 3, 3, 2, 2, 1, and 1. For some applications, to increase or decrease the PPT by less than 1 in successive bursts, the control unit increases or decreases the PPT by non-integer values, and achieves the non-integer portion of the increase or decrease by setting a parameter of one or more pulses other than PPT, such as pulse duration or amplitude. For example, the first bursts of an "on" period may have respective PPTs of 0.5, 1, 1.5, 2, 2.5, and 3, and the last bursts of an "on" period may have respective PPTs of 3, 2.5, 2, 1.5, 1, and 0.5. To achieve the decimal portion of these PPTs, the control unit may apply a pulse having a pulse duration equal to the decimal portion of these PPTs times the pulse duration of a full pulse. For example, if the pulse duration of a full pulse is 1 ms, a commencement ramp of 0.5, 1, and 1.5 PPT may be achieved by applying a first burst consisting of a single 0.5 ms pulse, a second burst consisting of a single 1 ms pulse, and a third burst consisting of a 1 ms pulse followed by a 0.5 ms pulse. Alternatively, to achieve the decimal portion of these PPTs, the control unit may apply a pulse having a full pulse duration but an amplitude equal to the decimal portion of these PPTs times the amplitude of a full pulse. For example, if the pulse duration and amplitude of a full pulse if 1 ms and 3 mA, respectively, a commencement ramp of 0.5, 1, and 1.5 PPT may be achieved by apply a first burst consisting of a single 1 ms pulse having an amplitude of 1.5 mA, a second burst consisting of a single 1 ms, 3 mA pulse, and a third burst consisting of a 1 ms, 3 mA followed by a 1 ms pulse having an amplitude of 1.5 mA.

For some applications, control unit 32 is configured to synchronize the bursts with a feature of the cardiac cycle of the subject. For example, each of the bursts may commence after a delay after a detected R-wave, P-wave, or other feature of an ECG. Alternatively, for some applications, the control unit is configured to synchronize the bursts with other physiological activity of the subject, such as respiration, muscle contractions, or spontaneous nerve activity. For some applications, such ramping is applied only at the commencement of each "on" period 204, or only at the conclusion of each "on" period 204, rather than during both transitional periods.

For some applications, such ramping techniques are combined with the extended PRI techniques described hereinabove with reference to FIG. 6, and/or with the rest period techniques described hereinabove with reference to FIG. 7.

Although some embodiments of the present invention are described herein with respect to applying an electrical current to tissue of a subject, this is to be understood in the specification and in the claims as including creating a voltage drop between two or more electrodes.

In some embodiments of the present invention, techniques described herein for preventing and/or treating AF are used to prevent and/or treat atrial flutter, atrial premature beats (APBs), or other atrial arrhythmia.

Although embodiments of the present invention described hereinabove with reference to FIGS. 2A, 2B, 3 and 4 are described with reference to the vagus nerve, the electrode devices of these embodiments may also be applied to other nerves or nervous tissue for some applications, such as to the parasympathetic sites listed hereinabove.

The scope of the present invention includes embodiments described the references cited hereinabove in the Background of the Invention, and in the following applications, which are assigned to the assignee of the present application and are incorporated herein by reference. In an embodiment, techniques and apparatus described in one or more of the following applications are combined with techniques and apparatus described herein:

U.S. patent application Ser. No. 10/205,474, filed Jul. 24, 2002, entitled, "Electrode assembly for nerve control," which published as US Patent Application Publication 2003/0050677

U.S. Provisional Patent Application 60/383,157 to Ayal et al., filed May 23, 2002, entitled, "Inverse recruitment for autonomic nerve systems"

U.S. patent application Ser. No. 10/205,475, filed Jul. 24, 2002, entitled, "Selective nerve fiber stimulation for treating heart conditions," which published as US Patent Application Publication 2003/0045909

PCT patent application PCT/IL02/00068, filed Jan. 23, 2002, entitled, "Treatment of disorders by unidirectional nerve stimulation," which published as PCT Publication WO 03/018113, and U.S. patent application Ser. No. 10/488,334, filed Feb. 27, 2004, in the US National Phase thereof U.S. patent application Ser. No. 09/944,913, filed Aug. 31, 2001, entitled, "Treatment of disorders by unidirectional nerve stimulation," which issued as U.S. Pat. No. 6,684,105

U.S. patent application Ser. No. 10/461,696, filed Jun. 13, 2003, entitled, "Vagal stimulation for anti-embolic therapy," which published as US Patent Application Publication 2004/0254612

PCT Patent Application PCT/IL03/00430, filed May 23, 2003, entitled, "Electrode assembly for nerve control," which published as PCT Publication WO 03/099373

PCT Patent Application PCT/IL03/00431, filed May 23, 2003, entitled, "Selective nerve fiber stimulation for treating heart conditions," which published as PCT Publication WO 03/099377

U.S. patent application Ser. No. 10/719,659, filed Nov. 20, 2003, entitled, "Selective nerve fiber stimulation for treating heart conditions," which published as US Patent Application Publication 2004/0193231

PCT Patent Application PCT/IL04/00440, filed May 23, 2004, entitled, "Selective nerve fiber stimulation for treating heart conditions," which published as PCT Publication WO 04/103455

PCT Patent Application PCT/IL04/000496, filed Jun. 10, 2004, entitled, "Vagal stimulation for anti-embolic therapy," which published as PCT Publication WO 04/110550

U.S. patent application Ser. No. 10/866,601, filed Jun. 10, 2004, entitled, "Applications of vagal stimulation," which published as US Patent Application Publication 2005/0065553

PCT Patent Application PCT/IL04/000495, filed Jun. 10, 2004, entitled, "Applications of vagal stimulation," which published as PCT Publication WO 04/110549

U.S. patent application Ser. No. 11/022,011, filed Dec. 22, 2004, entitled, "Construction of electrode assembly for nerve control," which published as US Patent Application Publication 2006/0136024

U.S. patent application Ser. No. 11/062,324, filed Feb. 18, 2005, entitled, "Techniques for applying, calibrating, and controlling nerve fiber stimulation," which published as US Patent Application Publication 2005/0197675

U.S. patent application Ser. No. 11/064,446, filed Feb. 22, 2005, entitled, "Techniques for applying, configuring, and coordinating nerve fiber stimulation," which published as US Patent Application Publication 2005/0267542

U.S. patent application Ser. No. 11/280,884, filed Nov. 15, 2005, entitled, "Techniques for nerve stimulation," which published as US Patent Application Publication 2006/0106441

U.S. patent application Ser. No. 11/340,156, filed Jan. 25, 2006, entitled, "Method to enhance progenitor or genetically-modified cell therapy," which published as US Patent Application Publication 2006/0167501

U.S. patent application Ser. No. 11/359,266, filed Feb. 21, 2006, entitled, "Parasympathetic pacing therapy during and following a medical procedure, clinical trauma or pathology," which published as US Patent Application Publication 2006/0206155

U.S. patent application Ser. No. 10/745,514, filed Dec. 29, 2003, entitled, "Nerve-branch-specific action-potential activation, inhibition, and monitoring," which published as US Patent Application Publication 2005/0149154

U.S. patent application Ser. No. 11/234,877, filed Sep. 22, 2005, entitled, "Selective nerve fiber stimulation," which published as US Patent Application Publication 2006/0100668

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method comprising:
applying an electrical current, at a first strength on average, to a site of a subject containing parasympathetic nervous tissue;
configuring the current to stimulate the nervous tissue in the site;
performing at least one action selected from the group consisting of: sensing an occurrence of an episode of atrial fibrillation (AF), and predicting an imminent episode of the AF; and
responsively to the performing, applying the current at a second strength on average during a strength reduction period having a duration of at least one minute, which second strength is less than the first strength.

2. The method according to claim 1, comprising, upon a conclusion of the strength reduction period, configuring the current to reduce a heart rate of the subject, upon sensing that the episode of the AF has not terminated and that the subject has an elevated heart rate.

3. The method according to claim 1, wherein applying the current at the second strength comprises withholding applying the current.

4. The method according to claim 1, wherein applying the current at the first strength comprises applying the current at the first strength at least once during each of seven consecutive 48-hour periods.

5. The method according to claim 1, wherein the site is selected from the group consisting of: a vagus nerve, an epicardial fat pad, a sinoatrial (SA) node fat pad, an atrioventricular (AV) node fat pad, a pulmonary vein, a carotid artery, a carotid sinus, a coronary sinus, a vena cava vein, a jugular vein, an azygos vein, an innominate vein, and a subclavian vein, and wherein applying the current comprises applying the current to the selected site.

6. The method according to claim 1, wherein performing comprises sensing the occurrence of the episode of the AF, and wherein applying the current at the second strength comprises during the strength reduction period comprises applying the current at the second strength during the episode.

7. The method according to claim 6, wherein applying the current at the second strength responsively to the performing comprises applying the second current at the second strength upon sensing the occurrence of the episode of the AF.

8. The method according to claim 1, wherein performing comprises predicting the imminent episode of the AF.

9. The method according to claim 8, wherein applying the current at the second strength responsively to the performing comprises applying the second current at the second strength upon predicting the imminent episode of the AF.

10. The method according to claim 1, wherein the duration of the strength reduction period is at least one hour, and wherein applying the current at the second strength on average comprises applying the current at the second strength on average during the strength reduction period having the duration of at least one hour.

11. The method according to claim 1, comprising identifying that the subject is at risk of suffering from AF, wherein applying the current at the first strength comprises, responsively to the identifying, reducing a risk of the occurrence of the episode of the AF by applying the current at the first strength.

12. The method according to claim 11, wherein applying the current at the first strength comprises commencing applying at least 24 hours after the identifying.

13. The method according to claim 1, wherein applying the current at the first strength comprises detecting normal sinus rhythm (NSR) of the subject, and applying the current at the first strength during the detected NSR.

14. The method according to claim 1, wherein applying the current at the first strength does not comprise configuring the current to achieve a target heart rate or a target heart rate range of the subject.

15. Apparatus comprising:
an electrode device, configured to be coupled to a site of the subject at risk of suffering from atrial fibrillation (AF), the site containing parasympathetic nervous tissue; and
a control unit, configured to:
drive the electrode device to apply an electrical current to the site at a first strength on average,
configure the current to stimulate the nervous tissue in the site, perform at least one action selected from the group consisting of: sensing an occurrence of an episode of atrial fibrillation (AF), and predicting an imminent episode of the AF, and responsively to the performance, apply the current at a second strength on average during a strength reduction period having a duration of at least one minute, which second strength is less than the first strength.

16. The apparatus according to claim 15, wherein the control unit is configured to, upon a conclusion of the strength reduction period, configure the current to reduce a heart rate of the subject, upon sensing that the episode of the AF has not terminated and that the subject has an elevated heart rate.

17. The apparatus according to claim 15, wherein the control unit is configured to apply the current at the second strength by withholding applying the current.

18. The apparatus according to claim 15, wherein the control unit is configured to apply the current at the first strength at least once during each of seven consecutive 48-hour periods.

19. The apparatus according to claim 15, wherein the site is selected from the group consisting of: a vagus nerve, an epicardial fat pad, a sinoatrial (SA) node fat pad, a pulmonary vein, an atrioventricular (AV) node fat pad, a carotid artery, a carotid sinus, a coronary sinus, a vena cava vein, a jugular vein, an azygos vein, an innominate vein, and a subclavian vein, and wherein the electrode device is configured to be coupled to the selected site.

20. The apparatus according to claim 15, wherein the control unit is configured to sense the occurrence of the episode of the AF, and to apply the current at the second strength during the episode.

21. The apparatus according to claim 20, wherein the control unit is configured to apply the current at the second strength upon sensing the occurrence of the episode of the AF.

22. The apparatus according to claim 15, wherein the control unit is configured to predict the imminent episode of the AF.

23. The apparatus according to claim 22, wherein the control unit is configured to apply the current at the second strength upon predicting the imminent episode of the AF.

24. The apparatus according to claim 15, wherein the duration of the strength reduction period is at least one hour, and wherein the control unit is configured to apply the current at the second strength on average during the strength reduction period having the duration of at least one hour.

25. The apparatus according to claim 15, wherein the control unit is configured to reduce a risk of the occurrence of the episode of the AF by driving the electrode device to apply the current at the first strength.

26. The apparatus according to claim 15, wherein the control unit is configured to detect normal sinus rhythm (NSR) of the subject, and to drive the electrode device to apply the current at the first strength during the detected NSR.

27. The apparatus according to claim 15, wherein the control unit is not configured to configure the current to achieve a target heart rate or a target heart rate range of the subject.

* * * * *